(12) United States Patent
Oda

(10) Patent No.: US 11,723,618 B2
(45) Date of Patent: Aug. 15, 2023

(54) RADIOGRAPHIC IMAGE DETECTION DEVICE, METHOD FOR OPERATING RADIOGRAPHIC IMAGE DETECTION DEVICE, AND PROGRAM FOR OPERATING RADIOGRAPHIC IMAGE DETECTION DEVICE

(71) Applicant: FUJIFILM CORPORATION, Tokyo (JP)

(72) Inventor: Yasufumi Oda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 181 days.

(21) Appl. No.: 17/163,595

(22) Filed: Feb. 1, 2021

(65) Prior Publication Data
US 2021/0251593 A1     Aug. 19, 2021

(30) Foreign Application Priority Data
Feb. 13, 2020   (JP) ................................. 2020-022642

(51) Int. Cl.
*A61B 6/00*     (2006.01)
*G01T 1/20*     (2006.01)
(Continued)

(52) U.S. Cl.
CPC .......... *A61B 6/5258* (2013.01); *A61B 6/5264* (2013.01); *G01T 1/2018* (2013.01);
(Continued)

(58) Field of Classification Search
CPC .................................. A61B 6/46; A61B 6/52
See application file for complete search history.

(56) References Cited

U.S. PATENT DOCUMENTS

2013/0329981 A1   12/2013   Hiroike
2014/0296657 A1*  10/2014   Izmirli .................... A61B 5/06
                                                                 600/301
(Continued)

FOREIGN PATENT DOCUMENTS

JP       2006-75359 A     3/2006
JP       2013-255606 A   12/2013
(Continued)

OTHER PUBLICATIONS

EPO, Machine translation of specification of JP2014168602A (Year: 2022).*

(Continued)

*Primary Examiner* — David N Werner
(74) *Attorney, Agent, or Firm* — Solaris Intellectual Property Group, PLLC

(57) ABSTRACT

The radiographic image detection device performs: a radiographic image generation process of reading a pixel signal from a pixel region in a state in which radiation is emitted to generate a radiographic image; a first correction image acquisition process of reading the pixel signal from the pixel region a plurality of times to acquire a plurality of first correction images in a shorter accumulation time than the radiographic image or using binning reading in a state in which the radiation is not emitted immediately before radiography including the radiographic image generation process; a selection process of selecting, as an averaging target, at least two or more of the plurality of first correction images according to a time elapsed since immediately preceding radiography or an amount of variation in a residual image based on the first correction image; and a correction process of correcting the radiographic image on the basis of an average image obtained by averaging the first correction images selected as the averaging target.

9 Claims, 16 Drawing Sheets

(51) Int. Cl.
*H04N 5/32* (2023.01)
*H04N 25/40* (2023.01)

(52) U.S. Cl.
CPC ............... *H04N 5/32* (2013.01); *H04N 25/40* (2023.01); *A61B 6/5235* (2013.01); *A61B 6/5241* (2013.01); *A61B 6/542* (2013.01); *A61B 6/582* (2013.01)

(56) References Cited

U.S. PATENT DOCUMENTS

| | | | |
|---|---|---|---|
| 2016/0089097 A1* | 3/2016 | Oh | A61B 6/504 345/590 |
| 2016/0316547 A1 | 10/2016 | Wayama et al. | |
| 2016/0354047 A1* | 12/2016 | Huston | A61B 6/5288 |
| 2018/0303454 A1* | 10/2018 | Issani | A61B 6/467 |
| 2018/0310898 A1* | 11/2018 | Ahn | A61B 6/42 |
| 2019/0015056 A1* | 1/2019 | Sato | A61B 6/5264 |
| 2019/0302278 A1 | 10/2019 | Tamura | |
| 2019/0320996 A1* | 10/2019 | Fetterly | A61B 6/5205 |
| 2021/0093277 A1* | 4/2021 | Jackson | A61B 5/7292 |
| 2021/0196219 A1* | 7/2021 | Jansen | G06T 11/008 |

FOREIGN PATENT DOCUMENTS

| | | |
|---|---|---|
| JP | 2014-168602 A | 9/2014 |
| JP | 2016-208498 A | 12/2016 |
| JP | 2019-170539 A | 10/2019 |
| JP | 2019-216875 A | 12/2019 |

OTHER PUBLICATIONS

EPO, Machine translation of specification of JP2019216875A (Year: 2022).*

English language translation of the following: Office action dated Dec. 20, 2022 from the JPO in a Japanese patent application No. 2020-022642 corresponding to the instant patent application. This office action translation is submitted now in order to supplement the understanding of the cited references which are being disclosed in the instant Information Disclosure Statement.

* cited by examiner

RADIOGRAPHIC IMAGE DETECTION DEVICE, METHOD FOR OPERATING RADIOGRAPHIC IMAGE DETECTION DEVICE, AND PROGRAM FOR OPERATING RADIOGRAPHIC IMAGE DETECTION DEVICE

CROSS-REFERENCE TO RELATED APPLICATIONS

The present application claims priority under 35 U.S.C. § 119 to Japanese Patent Application No., 2020-022642 filed on Feb. 13, 2020. The above application is hereby expressly incorporated by reference, in its entirety, into the present application.

BACKGROUND

1. Technical Field

The technology of the present disclosure relates to a radiographic image detection device, a method for operating the radiographic image detection device, and a program for operating the radiographic image detection device.

2. Description of the Related Art

In the medical field, an X-ray imaging system that uses, for example, X-rays as radiation is known. The X-ray imaging system includes an X-ray generation apparatus that generates X-rays and an X-ray imaging apparatus that detects the X-rays, which have been generated by the X-ray generation apparatus and transmitted through a patient as a subject, to capture a radiographic image. The X-ray imaging apparatus includes an X-ray image detection device that detects an X-ray image based on the X-rays transmitted through the subject and a console that performs, for example, the control of the driving of the X-ray image detection device and the storage and display of the X-ray image.

The X-ray image detection devices include a direct conversion type that directly converts X-rays into charge and an indirect conversion type that converts X-rays into visible light and then converts the visible light into charge. In any of the types, the X-ray image detection device has a pixel region in which a plurality of pixels detecting X-rays are arranged and a reading unit that reads a pixel signal from the pixel region, and generates an X-ray image on the basis of the pixel signal read by the reading unit.

The X-ray image detected by the X-ray image detection device includes, for example, dark current noise generated in each pixel and fixed pattern noise generated by a charge amplifier and the like included in the reading unit. Offset data is acquired in advance before X-ray imaging in order to remove the noise components from the X-ray image. The offset data is acquired by reading the pixel signal from the pixel region in a state in which no X-rays are emitted. The offset data is data including only noise components. After the offset data is acquired, offset correction for subtracting the offset data from the X-ray image obtained by the X-ray imaging is performed to obtain an X-ray image from which noise has been removed.

Of the dark current noise and the fixed pattern noise included in the offset data, the dark current noise changes depending on the temperature. Therefore, a time interval from the acquisition of the offset data to the X-ray imaging is long. In a case in which the temperature changes during the time, a dark current noise component changes, which results in a reduction in the accuracy of offset correction. For this reason, it is ideal to acquire the offset data immediately before the X-ray imaging is performed, in order to improve the accuracy of offset correction.

However, in a case in which the offset data is acquired immediately before the X-ray imaging, a time lag occurs between the instruction to perform the X-ray imaging and the actual X-ray imaging. As a result, there is a possibility that the X-ray image intended by the radiographer will not be obtained. Therefore, a technique has been proposed in which an X-ray image detection device is driven in a time shorter than the irradiation time of X-ray imaging or in a binning mode to perform an offset data acquisition operation immediately before the X-ray imaging (see JP2014-168602A).

In addition, a technique has been proposed in which an average value of a plurality of offset data items obtained by acquiring offset data a plurality of times is used for offset correction in order to further improve the accuracy of offset correction (see JP2019-216875A). The plurality of offset data items are averaged to reduce random noise.

SUMMARY

A configuration is considered which applies the technique described in JP2019-216875A to the technique described in JP2014-168602A to acquire a plurality of offset data items (hereinafter, referred to as a correction image) immediately before X-ray imaging. In this case, the amount of noise becomes smaller as the number of acquired correction images becomes larger. Therefore, a high-quality correction image is obtained. However, in a case in which the number of acquired correction images increases, there is a possibility that the correction image will be affected by a residual image generated in the previous X-ray imaging.

The residual image can occur in the X-ray image detection devices of both the direct conversion type and the indirect conversion type. In the case of the indirect conversion type, the residual image is a phenomenon occurring since the light emission characteristics of a scintillator layer converting X-rays into visible light are changed by the high energy of incident X-rays and the influence of the previous X-ray imaging remains in the scintillator layer until the next X-ray imaging.

The technology of the present disclosure relates to a radiographic image detection device that can improve the accuracy of offset correction and suppress the influence of a residual image, a method for operating the radiographic image detection device, and a program for operating the radiographic image detection device.

In order to achieve the above object, according to an aspect of the present disclosure, there is provided a radiographic image detection device comprising: a pixel region in which a plurality of pixels detecting radiation are arranged; a reading unit that reads a pixel signal from the pixel region; and at least one processor. The processor performs: a radiographic image generation process of reading the pixel signal from the pixel region in a state in which the radiation is emitted to generate a radiographic image; a first correction image acquisition process of reading the pixel signal from the pixel region a plurality of times to acquire a plurality of first correction images in a shorter accumulation time than the radiographic image or using binning reading in a state in which the radiation is not emitted immediately before radiography including the radiographic image generation process; a selection process of selecting, as an averaging target, at least two or more of the plurality of first correction images according to a time elapsed since immediately preceding radiography or an amount of variation in a residual image based on the first correction image; and a correction process of correcting the radiographic image on the basis of an average image obtained by averaging the first correction images selected as the averaging target.

Preferably, in the selection process, the processor selects, as the averaging target, the first correction image acquired for a period for which the time elapsed since the immediately preceding radiography is equal to or greater than a predetermined value among the plurality of first correction images acquired by the first correction image acquisition process.

Preferably, in the selection process, the processor calculates a rate of change in the residual image over time on the basis of the plurality of first correction images acquired by the first correction image acquisition process and selects, as the averaging target, the first correction image acquired for a period for which the rate of change is equal to or less than a predetermined value.

Preferably, the processor performs a second correction image acquisition process of acquiring a second correction image using the same reading method as that used for the first correction image in a state in which the radiation is not emitted before the first correction image is acquired by the first correction image acquisition process. Preferably, in the correction process, the processor corrects the radiographic image on the basis of a difference image between the average image and the second correction image.

Preferably, the processor performs a third correction image acquisition process of acquiring a third correction image using the same reading method as that used for the radiographic image in a state in which the radiation is not emitted before the first correction image is acquired by the first correction image acquisition process. Preferably, in the correction process, the processor corrects the radiographic image on the basis of the third correction image and the difference image.

Preferably, the processor acquires the second correction image using the second correction image acquisition process immediately before the third correction image is acquired by the third correction image acquisition process.

Preferably, in the correction process, the processor subtracts the difference image and the third correction image from the radiographic image after performing, on the difference image, an accumulation time multiplication process or an enlargement and reduction process for adjusting an image size to the radiographic image and a process of multiplying a conversion coefficient corresponding to a difference between the reading methods.

Preferably, the processor performs the reading in a state in which gates of the plurality of pixels are turned off to generate the second correction image and the third correction image, and performs the reading in a state in which the gates of the plurality of pixels are turned on to generate the first correction image.

According to another aspect of the present disclosure, there is provided a method for operating a radiographic image detection device including a pixel region in which a plurality of pixels detecting radiation are arranged and a reading unit that reads a pixel signal from the pixel region. The method comprises: a radiographic image generation step of reading the pixel signal from the pixel region in a state in which the radiation is emitted to generate a radiographic image; a first correction image acquisition step of reading the pixel signal from the pixel region a plurality of times to acquire a plurality of first correction images in a shorter accumulation time than the radiographic image or using binning reading in a state in which the radiation is not emitted immediately before radiography including the radiographic image generation step; a selection step of selecting, as an averaging target, at least two or more of the plurality of first correction images according to a time elapsed since immediately preceding radiography or an amount of variation in a residual image based on the first correction image; and a correction step of correcting the radiographic image on the basis of an average image obtained by averaging the first correction images selected as the averaging target.

According to still another aspect of the present disclosure, there is provided an operation program for operating a radiographic image detection device comprising a pixel region in which a plurality of pixels detecting radiation are arranged, a reading unit that reads a pixel signal from the pixel region, and at least one processor. The operation program causes the processor to perform: a radiographic image generation process of reading the pixel signal from the pixel region in a state in which the radiation is emitted to generate a radiographic image; a first correction image acquisition process of reading the pixel signal from the pixel region a plurality of times to acquire a plurality of first correction images in a shorter accumulation time than the radiographic image or using binning reading in a state in which the radiation is not emitted immediately before radiography including the radiographic image generation process; a selection process of selecting, as an averaging target, at least two or more of the plurality of first correction images according to a time elapsed since immediately preceding radiography or an amount of variation in a residual image based on the first correction image; and a correction process of correcting the radiographic image on the basis of an average image obtained by averaging the first correction images selected as the averaging target.

According to the technology of the present disclosure, it is possible to provide a radiographic image detection device that can improve the accuracy of offset correction and suppress the influence of a residual image, a method for operating the radiographic image detection device, and a program for operating the radiographic image detection device.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
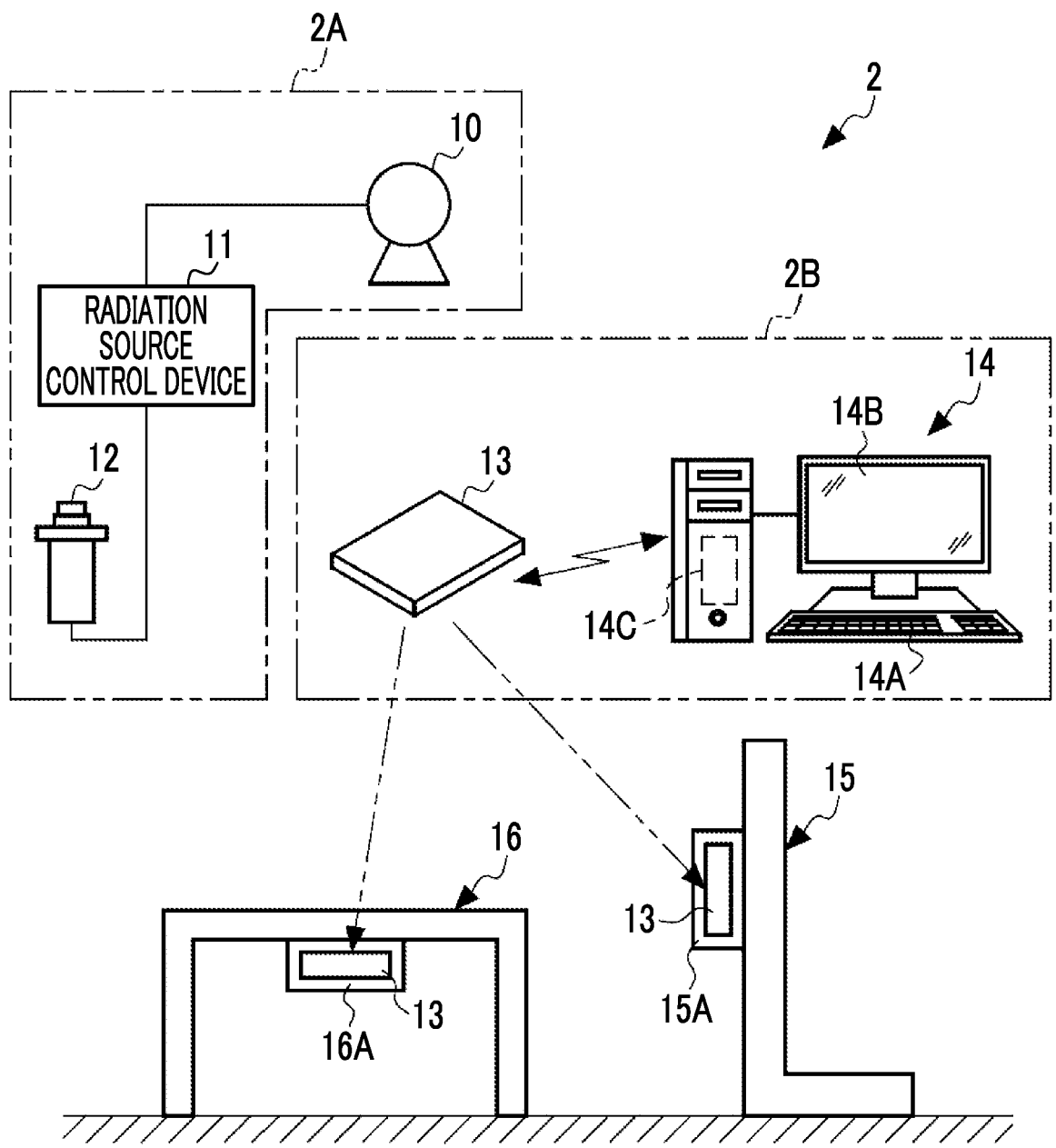
FIG. 1 is a schematic diagram illustrating a configuration of an X-ray imaging system.

In FIG. 1, an X-ray imaging system 2 includes an X-ray generation apparatus 2A and an X-ray imaging apparatus 2B. The X-ray generation apparatus 2A has an X-ray source 10, a radiation source control device 11, and an irradiation switch 12. The radiation source control device 11 controls the operation of the X-ray source 10. The irradiation switch 12 instructs the X-ray source 10 to start warm-up and irradiation with X-rays in response to an operation of an operator such as a radiology technician. In addition, the X-ray is an example of "radiation" according to the technology of the present disclosure.

The X-ray imaging apparatus 2B has an electronic cassette 13 and a console 14. The electronic cassette 13 is a portable X-ray image detection device. The console 14 controls the operation of the electronic cassette 13 and processes the display of an X-ray image. Further, the X-ray imaging system 2 is provided with, for example, an upright imaging stand 15 or a decubitus imaging stand 16. The upright imaging stand 15 is used in a case in which an image of the subject in an upright position is captured. The decubitus imaging stand 16 is used in a case in which an image of the subject in a decubitus position is captured. The electronic cassette 13 is set so as to be attachable to and detachable from a holder 15A of the upright imaging stand 15 or a holder 16A of the decubitus imaging stand 16. In addition, the X-ray image is an example of a "radiographic image" according to the technology of the present disclosure. Further, the electronic cassette 13 is an example of a "radiographic image detection device" according to the technology of the present disclosure.

Further, the X-ray imaging system 2 is provided with a radiation source movement device (not illustrated) that is used by the operator to move the X-ray source 10 in a desired direction and position. The radiation source movement device makes it possible to move the X-ray source 10 according to the imaging stand used for X-ray imaging. The operator can move the X-ray source 10 so as to face the upright imaging stand 15 or the decubitus imaging stand 16.

The X-ray generation apparatus 2A and the X-ray imaging apparatus 2B are not electrically connected to each other. That is, the X-ray imaging apparatus 2B is not a synchronous type that operates the electronic cassette 13 in synchronization with the start of irradiation with X-rays, but is an asynchronous type. Therefore, the electronic cassette 13 has an irradiation start detection function of detecting the start of irradiation with X-rays by the X-ray generation apparatus 2A.

As is well known, the X-ray source 10 includes an X-ray tube and an irradiation field limiter (collimator) that limits an irradiation field of X-rays emitted by the X-ray tube. The X-ray tube has a cathode which is a filament emitting thermoelectrons and an anode (target) which collides with the thermoelectrons emitted from the cathode and emits X-rays. In a case in which the X-ray source 10 receives an instruction to start warm-up, it starts preheating the filament and rotating the anode. The warm-up ends in a case in which the preheating of the filament is completed and the anode reaches a prescribed number of rotations.

The console 14 is connected to the electronic cassette 13 by a wired method or a wireless method so as to communicate therewith. The console 14 controls the operation of the electronic cassette 13 in response to an input operation of the operator through an input device 14A such as a keyboard. The X-ray image acquired by the electronic cassette 13 is displayed on a display 14B that is provided in the console 14. In addition, the X-ray image is stored in a storage device 14C, such as a hard disk or a flash memory provided in the console 14, or an image storage server (not illustrated) that is connected to the console 14 by a network.

Figure 2:
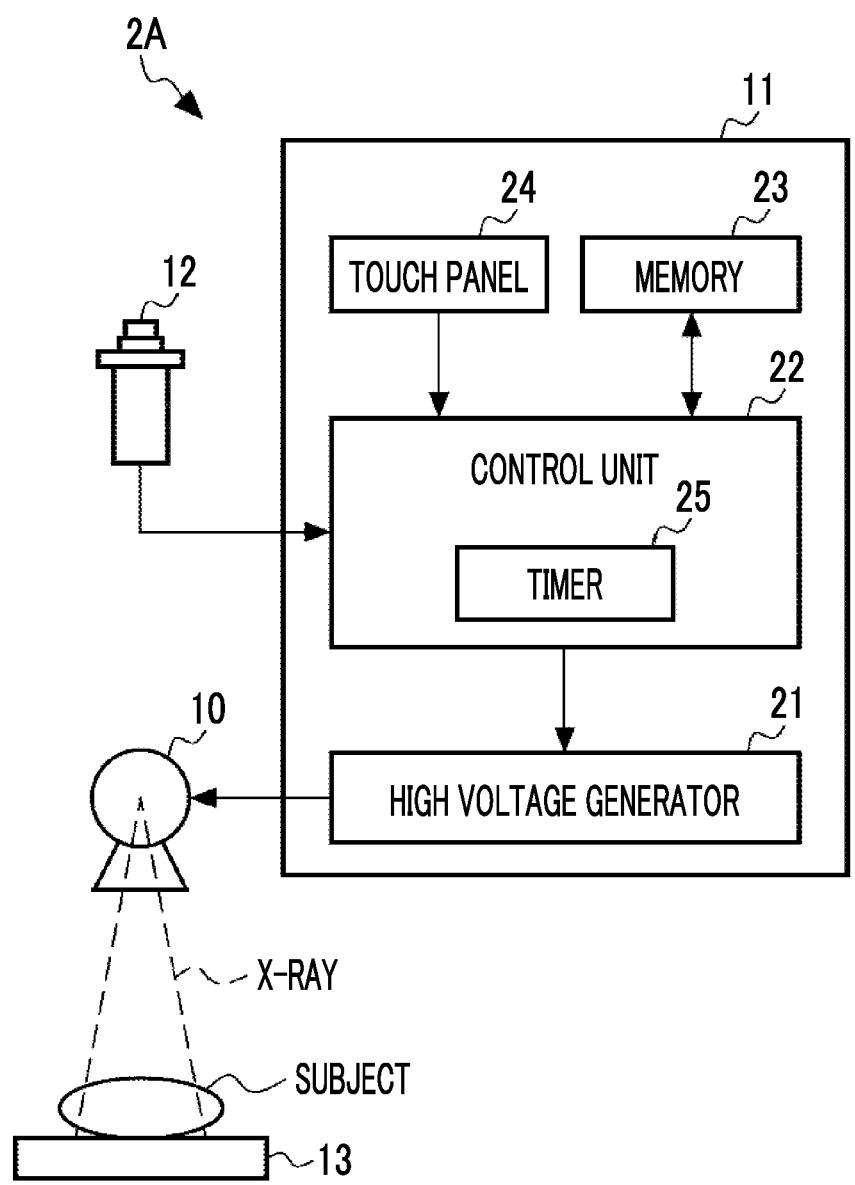
FIG. 2 is a schematic diagram illustrating a configuration of an X-ray generation apparatus.

In FIG. 2, the radiation source control device 11 includes a high voltage generator 21, a control unit 22, a memory 23, and a touch panel 24. The high voltage generator 21 boosts an input voltage with a transformer to generate a high voltage. The high voltage generated by the high voltage generator 21 is supplied as a tube voltage to the X-ray source 10 through a high voltage cable. The control unit 22 controls the tube voltage and a tube current supplied to the X-ray source 10 and an X-ray irradiation time.

The irradiation switch 12, the high voltage generator 21, the memory 23, and the touch panel 24 are connected to the control unit 22. The irradiation switch 12 is a switch that inputs an instruction to the control unit 22. The irradiation switch 12 is configured such that it can be pressed in two steps. In a case in which the irradiation switch 12 is pressed in one step (hereinafter, referred to as "halfway"), the control unit 22 outputs a warm-up instruction signal to the high voltage generator 21 to direct the X-ray source 10 to start warm-up. Further, in a case in which the irradiation switch 12 is pressed in two steps (hereinafter, referred to as "fully"), the control unit 22 outputs an irradiation instruction signal to the high voltage generator 21 to direct the X-ray source 10 to start irradiation with X-rays.

Like the storage device 14C of the console 14, the memory 23 stores in advance several types of imaging conditions including irradiation conditions, such as a tube voltage, a tube current, and an irradiation time. The operator manually sets the imaging conditions through the touch panel 24. A plurality of types of imaging conditions read from the memory 23 are displayed on the touch panel 24. The operator selects the same imaging conditions as the imaging conditions input to the console 14 from the displayed imaging conditions to set the imaging conditions in the radiation source control device 11. The control unit 22 is provided with a timer 25 for stopping the irradiation with X-rays in a case in which the set irradiation time comes.

Figure 3:
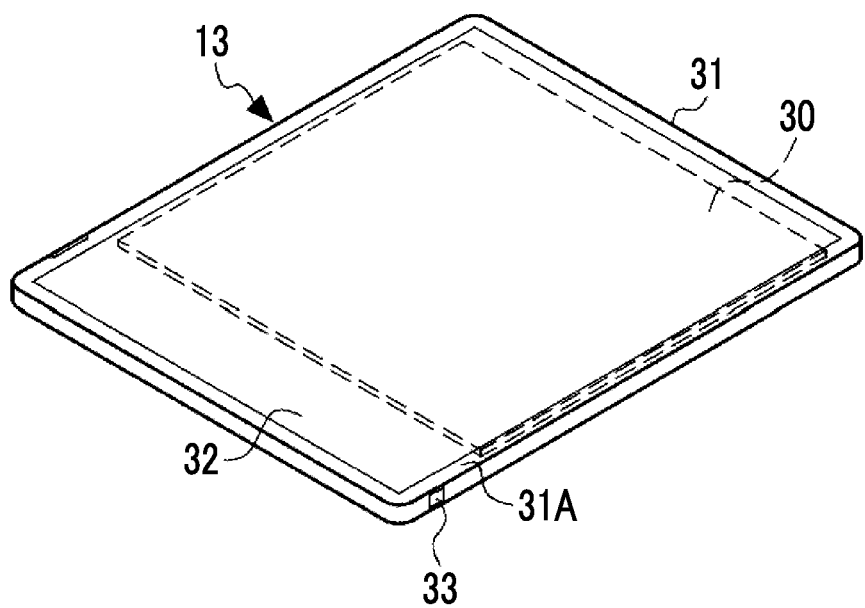
FIG. 3 is a perspective view illustrating an electronic cassette.

In FIG. 3, the electronic cassette 13 is an X-ray image detection device that detects X-rays transmitted through the subject and outputs an X-ray image. The electronic cassette 13 includes an image detection unit 30 and a housing 31. The housing 31 has a flat box shape and accommodates the image detection unit 30. The housing 31 is made of, for example, a conductive resin. In the housing 31, a rectangular opening is formed in a front surface 31A as an incident surface on which X-rays are incident, and an X-ray transmission plate 32 is attached to the opening. The X-ray transmission plate 32 is made of, for example, a carbon material that is lightweight and has high rigidity and high X-ray transparency.

The housing 31 also functions as an electromagnetic shield for preventing electromagnetic noise from entering the electronic cassette 13 and electromagnetic noise from being emitted from the electronic cassette 13 to the outside. In addition, a battery (for example, a secondary battery) that supplies power for driving the electronic cassette 13 and an antenna for performing wireless communication with the console 14 are provided in the housing 31.

For example, the housing 31 has a size conforming to the international standard ISO 4090:2001 which is substantially the same as that of a film cassette or an IP cassette. The electronic cassette 13 is set in the holder 15A of the upright imaging stand 15 or the holder 16A of the decubitus imaging stand 16 so as to be held in a posture in which the front surface 31A of the housing 31 faces the X-ray source 10. In addition, the electronic cassette 13 can be used in a state in which it is placed on the bed on which the subject lies supine, without using the upright imaging stand 15 and the decubitus imaging stand 16.

Figure 4:
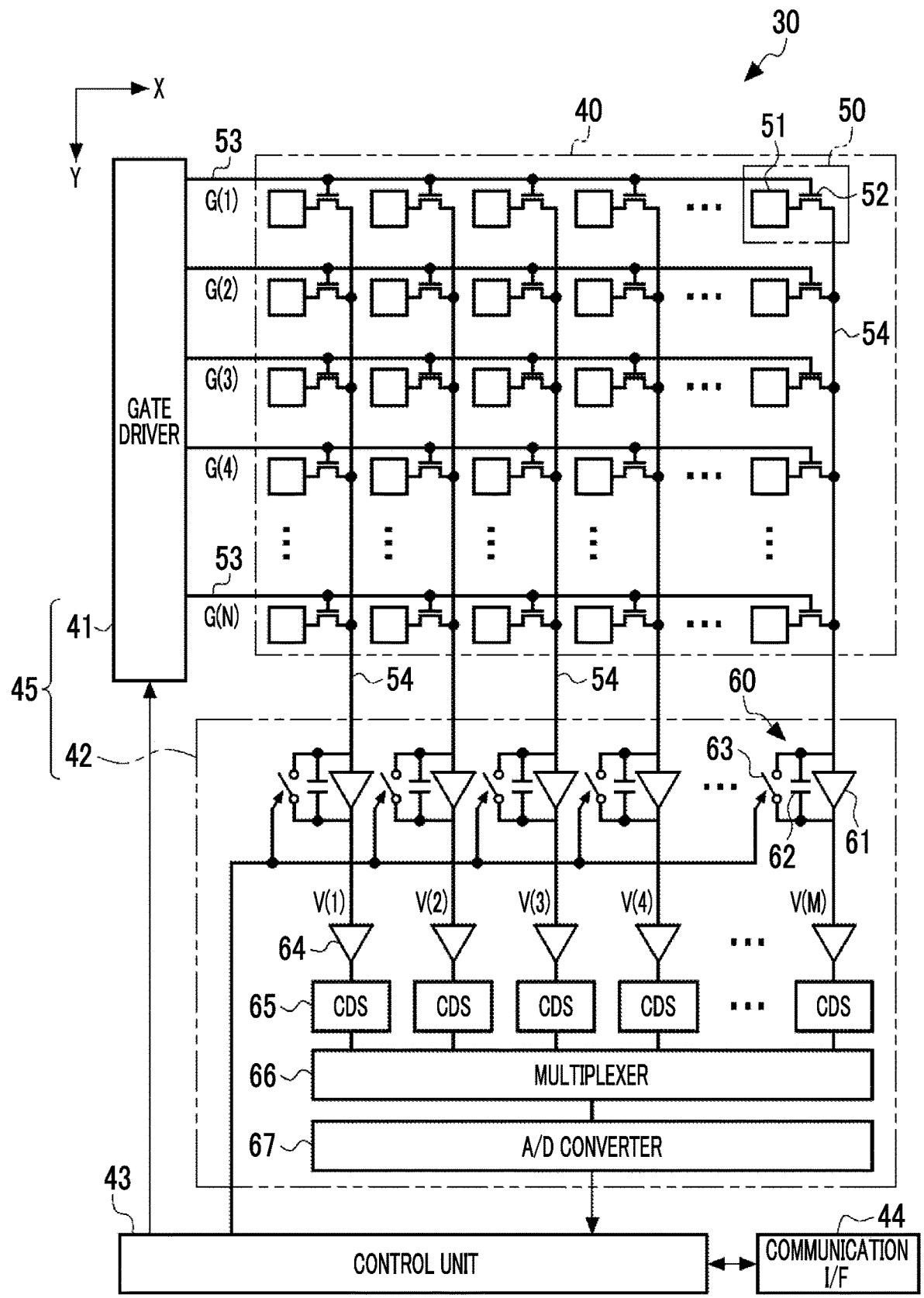
FIG. 4 is a diagram illustrating a configuration of an image detection unit.

In FIG. 4, the image detection unit 30 includes a pixel region 40, a gate driver 41, a signal processing circuit 42, a control unit 43, and a communication interface (I/F) 44. The gate driver 41 and the signal processing circuit 42 form a reading unit 45 that reads a pixel signal from the pixel region 40. The gate driver 41 and the signal processing circuit 42 are an example of a "reading unit" according to the technology of the present disclosure.

The pixel region 40 is formed on a thin film transistor (TFT) active matrix substrate. The pixel region 40 includes a plurality of pixels 50 that are arranged in a matrix along the X direction and the Y direction which are orthogonal to each other. It is assumed that the number of pixels 50 arranged in the X direction is M and the number of pixels 50 arranged in the Y direction is N. Each of N and M is an integer that is equal to or greater than 2. For example, each of N and M is about 2000. The array pattern of the pixels 50 is not limited to a square array, and may be a non-square array such as a so-called honeycomb array. The pixel 50 is an element that generates and accumulates charge according to the amount of incident X-rays.

The pixel region 40 is provided with a scintillator (not illustrated) that converts X-rays into visible light. The image detection unit 30 is an indirect conversion type in which photoelectric conversion is performed on the visible light converted by the scintillator in each pixel 50. The scintillator is made of, for example, CsI:Tl (thallium-activated cesium iodide) or $Gd_2O_2S$:Tb (terbium-activated gadolinium oxysulfide) and is disposed so as to face the entire surface of the pixel region 40. The image detection unit 30 is, for example, a penetration side sampling (PSS) type in which the scintillator and the TFT active matrix substrate are disposed in this order from an X-ray incident side. Further, the image detection unit 30 may be an irradiation side sampling (ISS) type in which the TFT active matrix substrate and the scintillator are disposed in this order from the X-ray incident side.

The image detection unit 30 is not limited to the indirect conversion type, but may be a direct conversion type using a conversion layer (for example, amorphous selenium) that directly converts X-rays into charge.

The pixel 50 includes a photoelectric conversion unit 51 that performs photoelectric conversion on the visible light converted by the scintillator to generate charge and accumulates the charge and a TFT 52 as a switching element. The photoelectric conversion unit 51 includes, for example, a p-intrinsic-n (PIN) semiconductor layer, an upper electrode that is disposed above the semiconductor layer, and a lower electrode that is disposed below the semiconductor layer. A bias voltage is applied to the upper electrode. The lower electrode is connected to the TFT 52.

The pixel region 40 includes N scanning lines 53 that extend in the X direction and M signal lines 54 that extend in the Y direction. The N scanning lines 53 and the M signal lines 54 are wired in a grid shape. Each pixel 50 is connected to an intersection portion of the scanning line 53 and the signal line 54. Specifically, in the pixel 50, a gate electrode of the TFT 52 is connected to the scanning line 53 and a source electrode of the TFT 52 is connected to the signal line 54. A drain electrode of the TFT 52 is connected to the photoelectric conversion unit 51.

Each scanning line 53 is commonly connected to M pixels 50 corresponding to one pixel row. Each signal line 54 is commonly connected to N pixels 50 corresponding to one pixel column. Each scanning line 53 is connected to the gate driver 41. Each signal line 54 is connected to the signal processing circuit 42.

The gate driver 41 outputs a gate pulse G(n) as a scanning signal to an n-th scanning line 53. Here, n is an integer from 1 to N. The gate pulse G(n) is applied to the gate electrodes of the TFTs 52 connected to the n-th scanning line 53. The TFT 52 is turned on in a case in which the voltage of the gate pulse G(n) is at a high level and is turned off in a case in which the voltage is at a low level. The time when the TFT 52 is turned on is defined by the width of the gate pulse G(n).

The charge accumulated in the photoelectric conversion unit 51 of the pixel 50 is output to the signal processing circuit 42 through the signal line 54 in a case in which the TFT 52 is turned on.

The signal processing circuit 42 includes an integrator 60 as a charge amplifier, an amplifier 64, a correlated double sampling (CDS) circuit 65, a multiplexer 66, and an analog/digital (A/D) converter 67. The integrator 60 is individually connected to each signal line 54. Each integrator 60 includes an operational amplifier 61, a capacitor 62, and a reset switch 63. The capacitor 62 and the reset switch 63 are connected in parallel between an input terminal and an output terminal of the operational amplifier 61. The signal line 54 is connected to the input terminal of the operational amplifier 61.

The integrator 60 integrates the charge input from the signal line 54, converts an integrated value into an analog voltage signal V(k), and outputs the analog voltage signal V(k). Here, k is an integer from 1 to M. The analog voltage signal V(k) corresponds to the integrated value of the charge input from a k-th signal line 54 to the integrator 60.

The output terminal of the operational amplifier 61 of each pixel column is connected to the input side of the multiplexer 66 through the amplifier 64 and the CDS circuit 65. The A/D converter 67 is connected to the output side of the multiplexer 66. The CDS circuit 65 has a sample-and-hold circuit. The CDS circuit 65 performs correlated double sampling on the analog voltage signal V(k) to remove a reset noise component.

The multiplexer 66 sequentially selects the connected M CDS circuits 65 and sequentially inputs the analog voltage signal V(k) subjected to the correlated double sampling to the A/D converter 67. In addition, the amplifier 64 is not limited to the configuration in which it is provided between the integrator 60 and the CDS circuit 65, but may be provided between the CDS circuit 65 and the A/D converter 67.

The A/D converter 67 sequentially converts the analog voltage signal V(k) input from the multiplexer 66 into a digital value and outputs the digital value as a pixel signal to the control unit 43. That is, the pixel signal is a signal corresponding to the amount of incident X-rays read from the pixel region 40 by the reading unit 45. The pixel signals corresponding to one frame which have been read from each pixel 50 of the pixel region 40 form an X-ray image.

The control unit 43 controls the operation of the reading unit 45 reading the pixel signal from the pixel region 40 to perform an X-ray imaging process, and performs a process of generating an X-ray image based on the read pixel signal. Further, the control unit 43 performs a correction image acquisition process of acquiring a correction image as offset data in a state in which no X-rays are emitted and a correction process of correcting the X-ray image on the basis of the acquired correction image, which will be described in detail below. Furthermore, the control unit 43 performs the above-mentioned irradiation start detection process.

The communication I/F 44 is connected to the console 14 (see FIG. 1) wirelessly or in a wired manner, and transmits and receives data to and from the console 14. For example, the communication I/F 44 receives data including imaging conditions transmitted from the console 14 and transmits data indicating the X-ray image generated by the control unit 43 to the console 14. The imaging conditions include the irradiation time determined corresponding to, for example, an imaging part.

Figure 5:
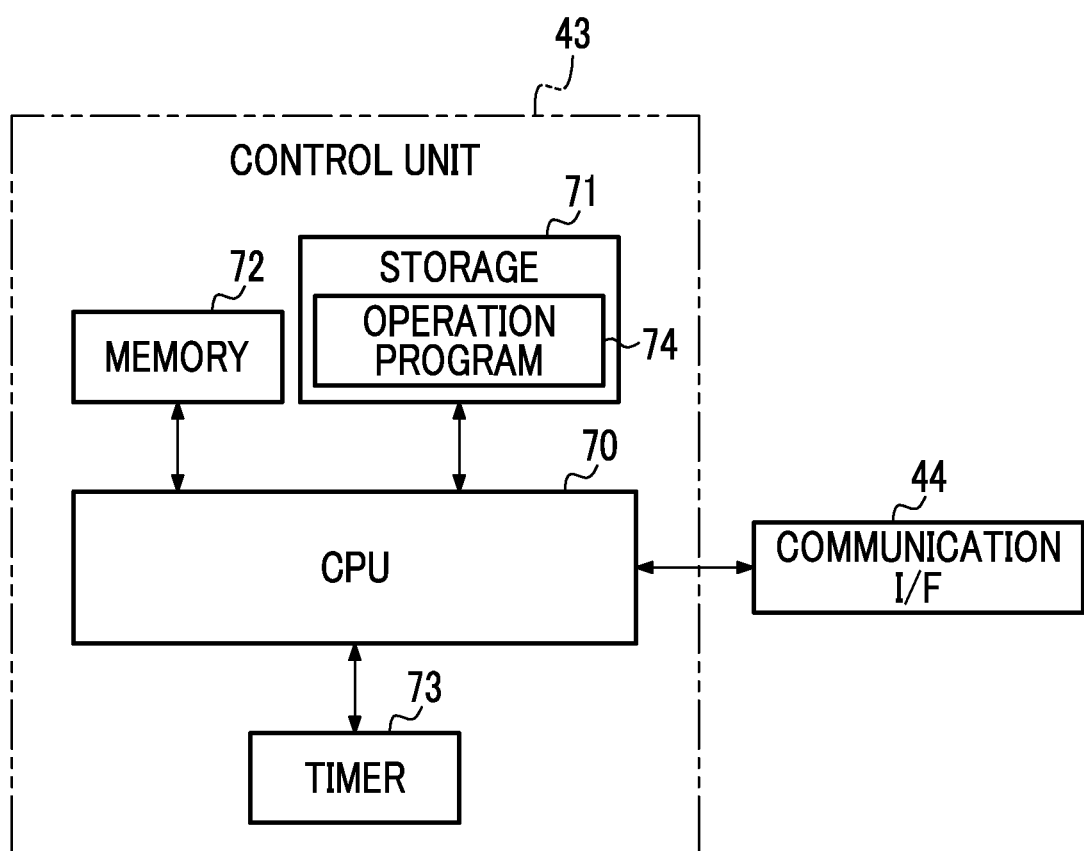
FIG. 5 is a block diagram illustrating a configuration of a control unit.

In FIG. 5, the control unit 43 of the image detection unit 30 includes, for example, a central processing unit (CPU) 70, a storage 71, a memory 72, and a timer 73. The storage 71 stores an operation program 74 and various kinds of data. The storage 71 is a non-volatile storage device such as a flash memory. The memory 72 is a volatile storage device, such as a random access memory (RAM) and is used as a work memory. The timer 73 is a timing device that measures time such as the irradiation time. The CPU 70 operates each unit on the basis of the operation program 74 to implement various functions. The CPU 70 is an example of a "processor" according to the technology of the present disclosure.

Figure 6:
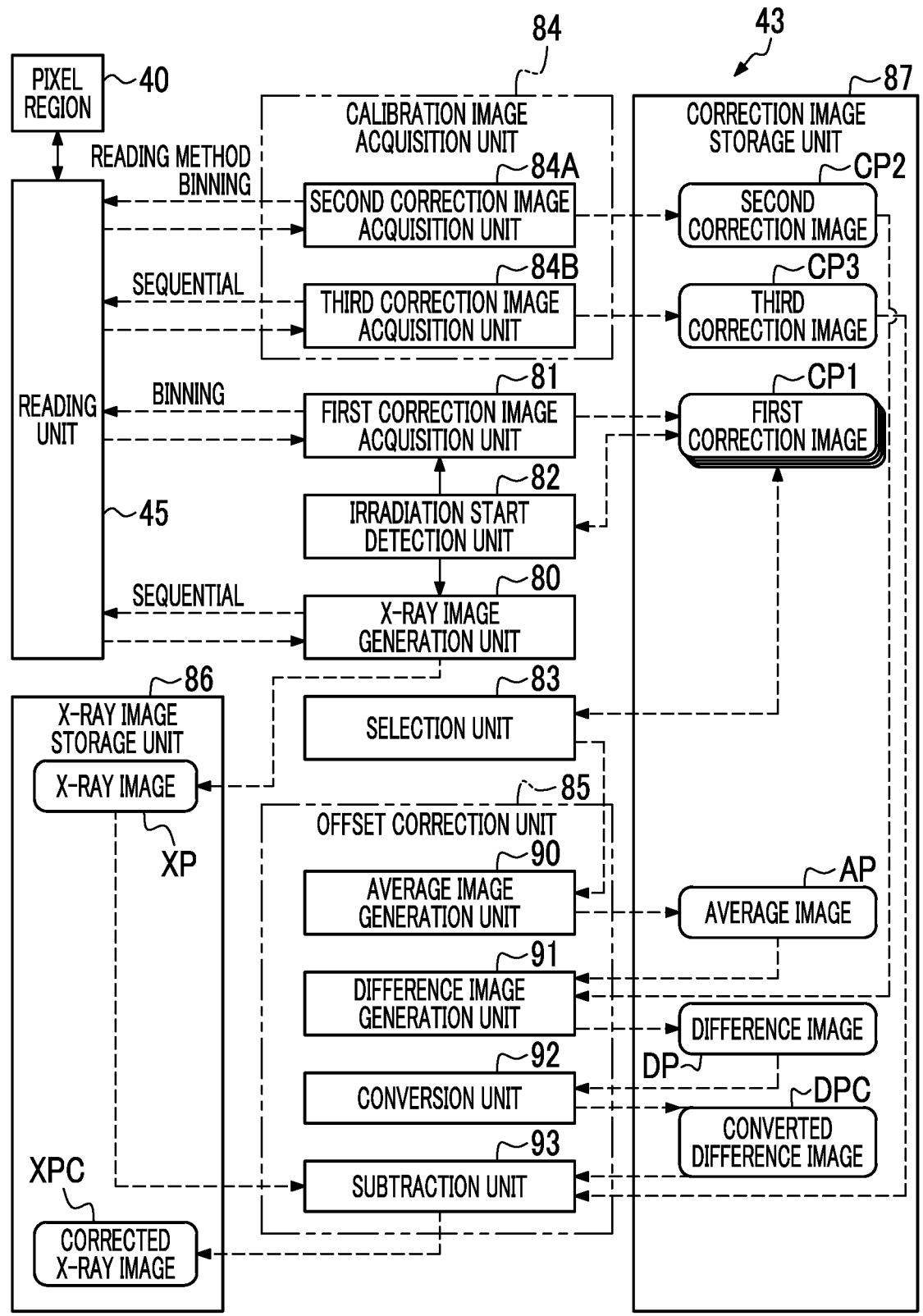
FIG. 6 is a block diagram illustrating functions implemented by the control unit.

FIG. 6 illustrates various functional units that are implemented in the control unit 43 by the CPU 70. In FIG. 6, an X-ray image generation unit 80, a first correction image acquisition unit 81, an irradiation start detection unit 82, a selection unit 83, a calibration image acquisition unit 84, and an offset correction unit 85 are implemented in the control unit 43. Each of an X-ray image storage unit 86 and a correction image storage unit 87 is implemented using the storage 71 and/or the memory 72.

Figure 7:
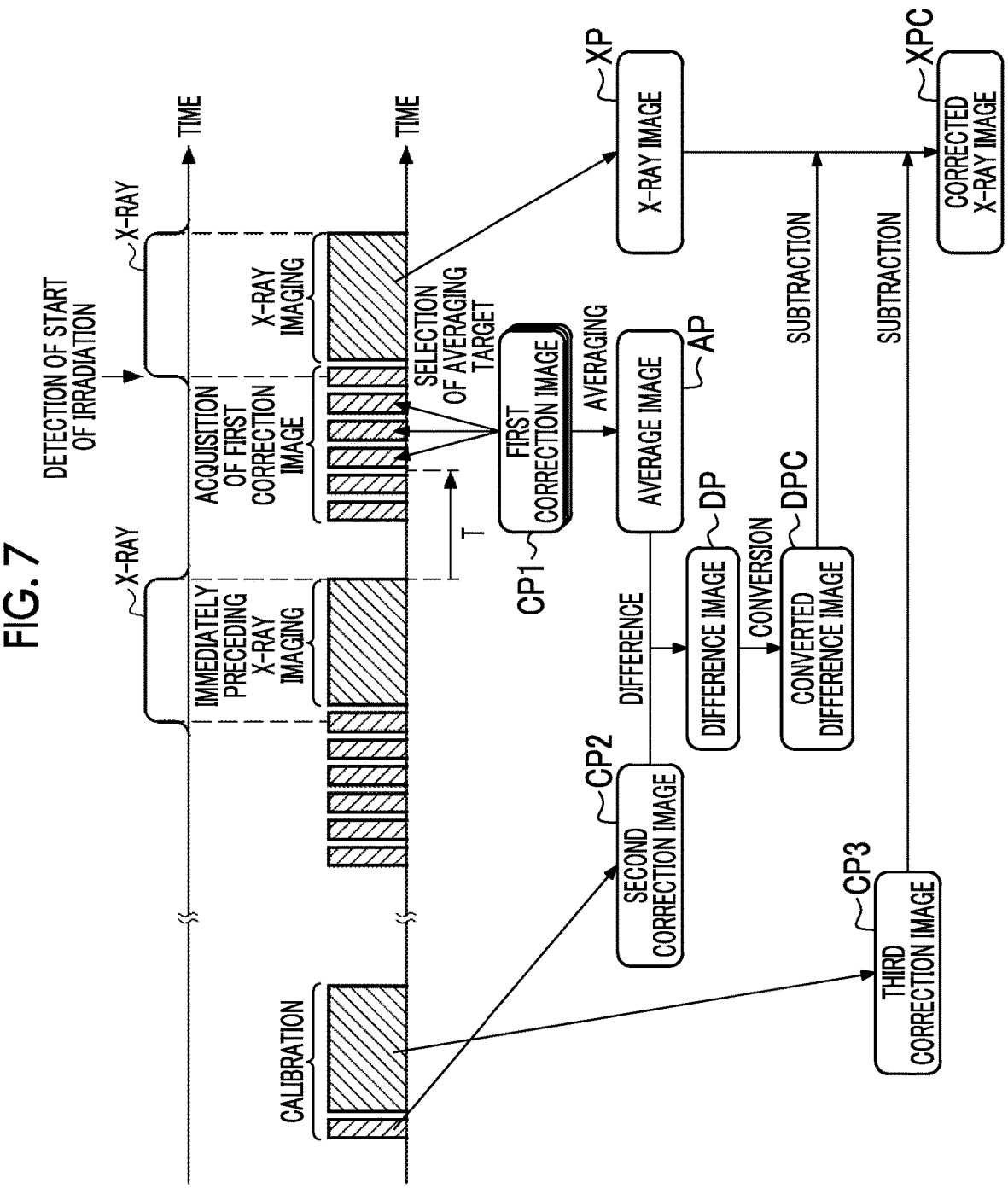
FIG. 7 is a schematic diagram illustrating a process performed by the control unit.

As illustrated in FIG. 7, the X-ray image generation unit 80 operates during X-ray imaging that is performed in a state in which X-rays are emitted. After the pixel region 40 is irradiated with the X-rays generated by the X-ray generation apparatus 2A through the subject, the X-ray image generation unit 80 drives the reading unit 45 to read pixel signals from the pixel region 40. Then, the X-ray image generation unit 80 generates an X-ray image XP on the basis of the read pixel signals. That is, the X-ray image generation unit 80 performs an X-ray image generation process.

Figure 8:
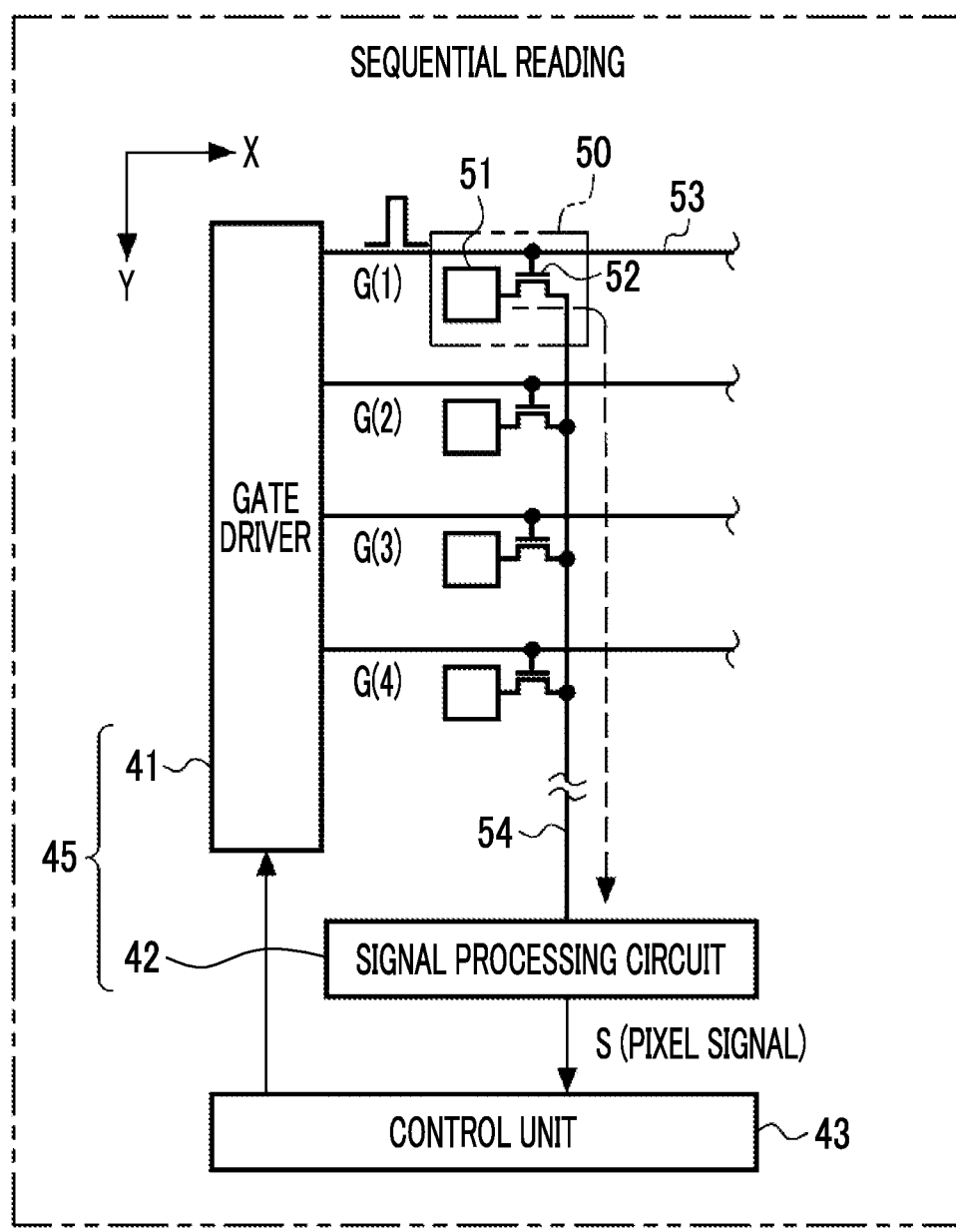
FIG. 8 is a diagram illustrating a sequential reading method.

The X-ray image generation unit 80 drives the reading unit 45 using a "sequential reading method" which sequentially selects the scanning lines 53 and individually reads the charge accumulated in each pixel 50 included in the pixel region 40. As illustrated in FIG. 8, in the sequential reading method, the gate driver 41 sequentially applies the gate pulse to the N scanning lines 53 to sequentially select the scanning lines 53 and reads charge from the pixels 50 connected to the selected scanning line 53.

In the sequential reading method, the TFTs 52 connected to one scanning line 53, to which the gate pulse has been applied, are turned on, and charge is output from the photoelectric conversion units 51 connected to the TFTs 52 to the signal line 54. The charge output to the signal line 54 is subjected to signal processing by the signal processing circuit 42 and is input as a pixel signal S to the control unit 43. The X-ray image generation unit 80 generates the X-ray image XP on the basis of the pixel signals S corresponding to all of the pixels 50 included in the pixel region 40. The X-ray image generation unit 80 stores the generated X-ray image XP in the X-ray image storage unit 86.

As illustrated in FIG. 7, the first correction image acquisition unit 81 operates immediately before the X-ray imaging. The first correction image acquisition unit 81 drives the reading unit 45 in a state in which the pixel region 40 is not irradiated with the X-rays immediately before the X-ray imaging to read the pixel signals from the pixel region 40. Then, the first correction image acquisition unit 81 generates a first correction image CP1 on the basis of the read pixel signals. That is, the first correction image acquisition unit 81 performs a first correction image acquisition process. In addition, the first correction image acquisition unit 81 performs the first correction image acquisition process a plurality of times immediately before the X-ray imaging to acquire a plurality of first correction images CP1. The first correction image acquisition unit 81 stores the acquired plurality of first correction images CP1 in the correction image storage unit 87.

Figure 9:
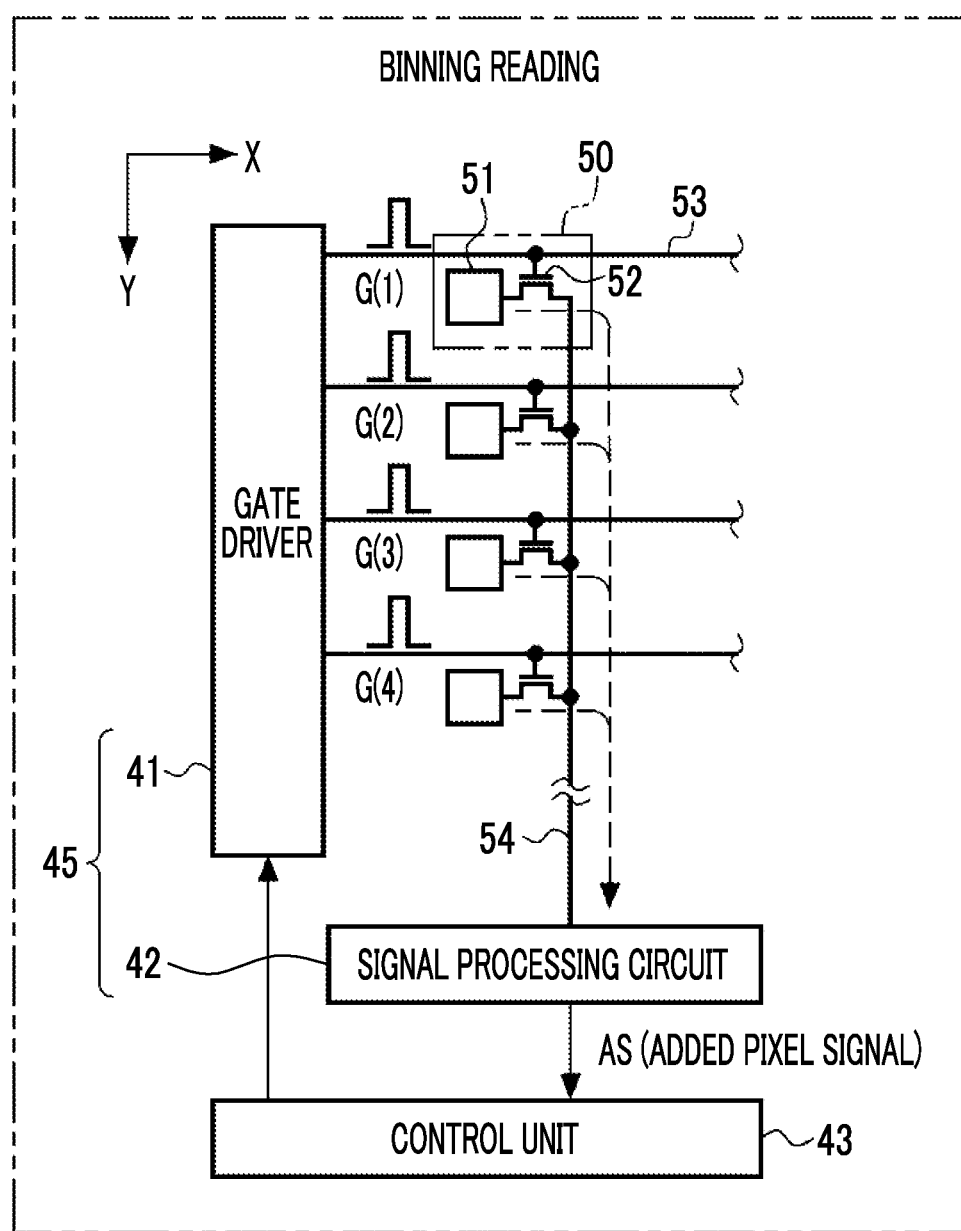
FIG. 9 is a diagram illustrating a binning reading method.

The first correction image acquisition unit 81 drives the reading unit 45 using a "binning reading method" that simultaneously selects a plurality of scanning lines 53 adjacent to each other, adds the charge accumulated in a plurality of pixels 50 included in the pixel region 40, and reads the added charge. As illustrated in FIG. 9, in the binning reading method, the N scanning lines 53 are divided into sets of four scanning lines 53, and the gate driver 41 simultaneously applies the gate pulse to each set of four scanning lines 53, adds charge corresponding to four pixels, and reads the added charge. In addition, the number of pixels added by the binning reading is not limited to four pixels.

In the binning reading method, the TFTs 52 connected to the plurality of scanning lines 53, to which the gate pulses have been applied, are turned on, and charge is output from the photoelectric conversion units 51 connected to the TFTs 52 to the signal lines 54. A plurality of charges output from a plurality of pixels 50 connected to the same signal line 54 are added on the signal line 54 and are then input to the signal processing circuit 42. The charge input to the signal processing circuit 42 is subjected to signal processing and is input to as an added pixel signal AS to the control unit 43. The first correction image acquisition unit 81 generates the first correction image CP1 on the basis of the added pixel signal AS corresponding to each addition pixel included in the pixel region 40. In addition, the addition pixels indicate a plurality of pixels 50 from which charge is added. In this embodiment, as illustrated in FIG. 9, four pixels 50 arranged in the Y direction are the addition pixels.

Figure 10:
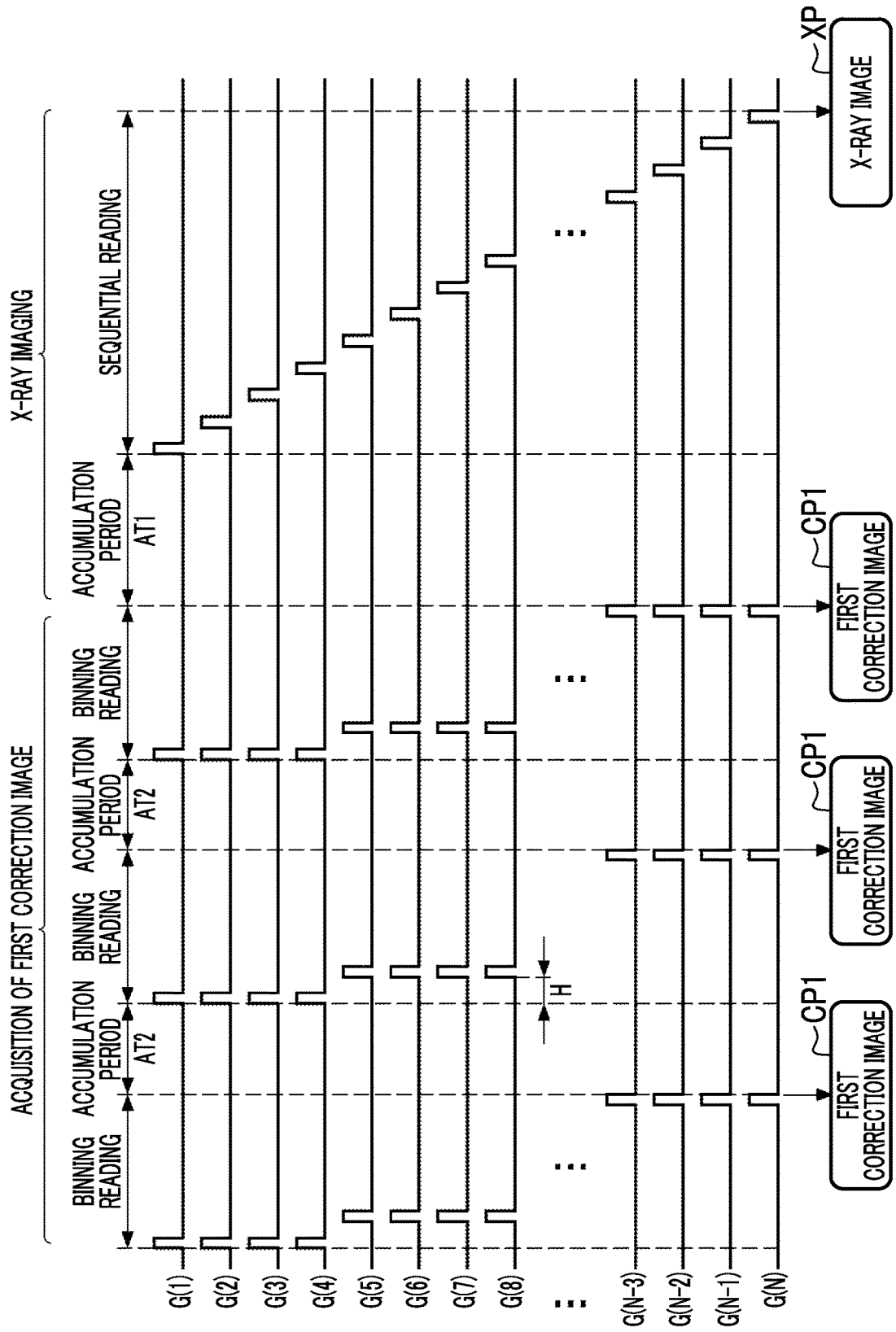
FIG. 10 is a timing chart illustrating gate pulses during sequential reading and binning reading.

As illustrated in FIG. 10, in the sequential reading performed during the X-ray imaging, the scanning lines 53 are sequentially selected one by one. In contrast, in the binning reading performed during the acquisition of the first correction image, the scanning lines 53 are sequentially selected four by four. Therefore, in this embodiment, the read time in the binning reading method is about one fourth of the read time in the sequential reading method.

Further, since the operation of the first correction image acquisition unit 81 acquiring the first correction image CP1 is performed immediately before the X-ray imaging, it also functions as a reset operation of discarding the charge accumulated in the pixel region 40 immediately before the X-ray imaging. Therefore, a charge accumulation period (hereinafter, simply referred to as an "accumulation period") AT1 in the X-ray imaging corresponds to a period from the end of the binning reading immediately before the X-ray imaging to the start of the sequential reading. During the accumulation period AT1, charge corresponding to the amount of X-rays emitted is mainly accumulated in the pixel region 40.

In the operation of acquiring the first correction image CP1, the binning reading is periodically repeated. Therefore, an accumulation period AT2 in the operation of acquiring the first correction image CP1 corresponds to a period from the end of the binning reading to the start of the next binning reading. During the accumulation period AT2, the charge caused by the dark current generated in each pixel 50 is mainly accumulated in the pixel region 40. The dark current is a noise component that is generated in a case in which no X-rays are emitted and is mainly caused by heat. In addition, during the accumulation period AT1, in addition to the charge corresponding to the amount of X-rays emitted, the charge caused by the dark current is accumulated in the pixel region 40.

The accumulation period AT2 may have the same length as the accumulation period AT1. However, in this embodiment, the accumulation period AT2 is set to be shorter than the accumulation period AT1 in order to shorten the acquisition time of the first correction image CP1 (that is, AT2<AT1). In this embodiment, since the pixel signal is read by the binning reading method during the operation of acquiring the first correction image CP1, the first correction image CP1 can be acquired in a shorter time than the X-ray image XP. Furthermore, since AT2<AT1 is satisfied, the first correction image CP1 can be acquired in a shorter time.

Figure 11:
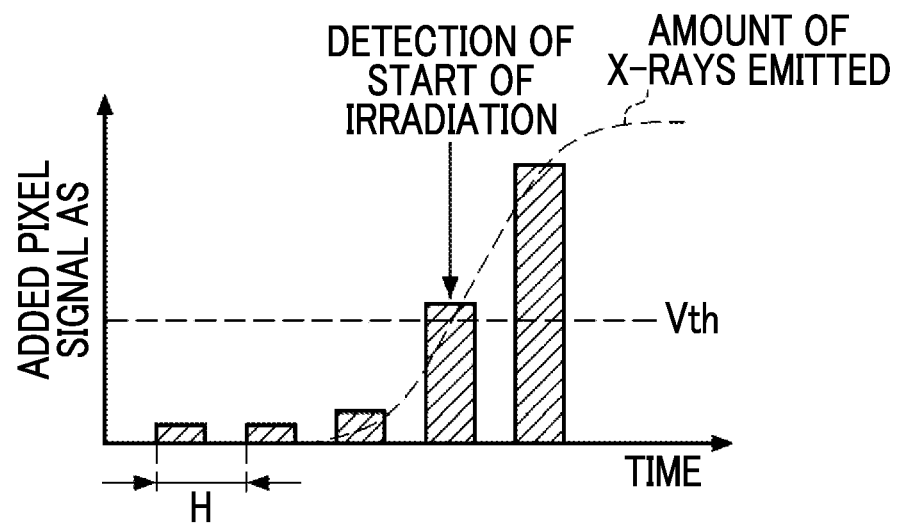
FIG. 11 is a diagram illustrating an irradiation start determination process.

Returning to FIG. 6, the irradiation start detection unit 82 detects that the X-ray generation apparatus 2A has started irradiation with X-rays on the basis of the first correction image CP1 acquired by the first correction image acquisition unit 81. Specifically, the irradiation start detection unit 82 monitors the signal value of the added pixel signal AS read by the binning reading during the operation of acquiring the first correction image CP1, as illustrated in FIG. 11. The irradiation start detection unit 82 determines that irradiation with X-rays has been started in a case in which the signal value of the added pixel signal AS is equal to or greater than a threshold value Vth. For example, the irradiation start detection unit 82 performs irradiation start detection every selection switching time H of the scanning line 53 (see FIG. 10). The selection switching time H is the time interval of the gate pulse output from the gate driver 41.

For example, the irradiation start detection unit 82 performs the irradiation start detection on the basis of the added pixel signal AS obtained through one signal line 54. In addition, the irradiation start detection unit 82 may perform the irradiation start detection on the basis of the maximum value of the added pixel signals AS obtained through a plurality of signal lines 54 for each pixel row. Further, the irradiation start detection unit 82 may perform the irradiation start detection on the basis of an average value or a sum, instead of the maximum value of the added pixel signals AS for each pixel row. Furthermore, the irradiation start detection unit 82 may perform the irradiation start detection on the basis of a difference value between the added pixel signals AS acquired every selection switching time H.

In a case in which the start of irradiation with X-rays has been detected, the irradiation start detection unit 82 notifies the first correction image acquisition unit 81 and the X-ray image generation unit 80 that the start of irradiation has been detected. In a case in which the notification is received from the irradiation start detection unit 82, the first correction image acquisition unit 81 stops the binning reading after the binning reading is performed on the final scanning line 53. In a case in which the notification is received from the irradiation start detection unit 82, the X-ray image generation unit 80 starts the measurement of the irradiation time from the time when the binning reading is stopped with the timer 73 (see FIG. 5). The irradiation time is a value that is included in the imaging conditions acquired by the control unit 43 from the console 14. The X-ray image generation unit 80 starts the sequential reading in a case in which the irradiation time has elapsed. The irradiation period corresponds to the accumulation period AT1.

Figure 12:
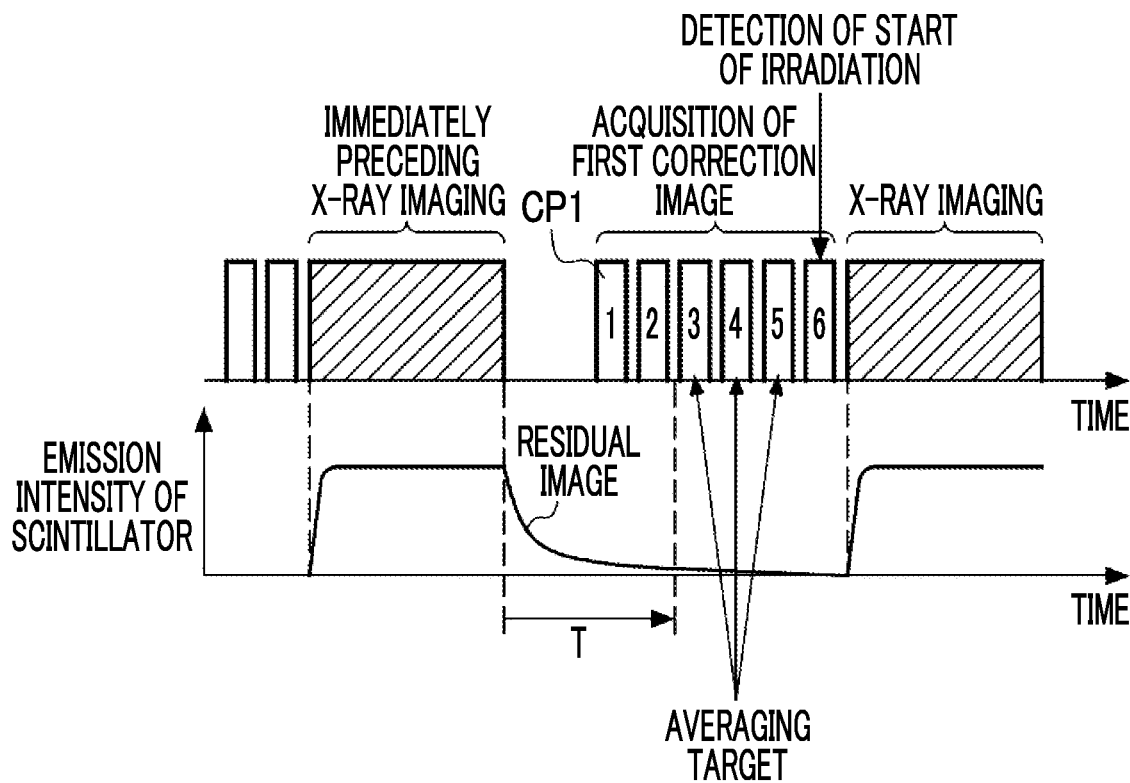
FIG. 12 is a diagram illustrating an averaging target selection process.

The selection unit 83 performs a selection process of selecting at least two or more first correction images CP1 which are actually used to correct the X-ray image XP from the plurality of first correction images CP1 acquired by the first correction image acquisition unit 81. Specifically, as illustrated in FIG. 12, the selection unit 83 measures the time elapsed since the time when the immediately preceding X-ray imaging ended (for example, the time when the sequential reading ended) with the timer 73. The selection unit 83 selects, as an averaging target, the first correction image CP1 acquired after a predetermined time T has elapsed since the time when the immediately preceding X-ray imaging ended. In addition, since the first correction image CP1 most immediately before the X-ray imaging is affected by irradiation with X-rays as illustrated in FIG. 11, it is excluded from the averaging target.

The scintillator provided in the pixel region 40 is irradiated with X-rays and emits light. However, light is emitted even after the irradiation with the X-rays is stopped. Hereinafter, an image formed by the remaining emitted light after the irradiation with the X-rays is referred to as a "residual image". The amount of the residual image is gradually reduced over time after the irradiation with the X-rays is stopped. The predetermined time T corresponds to the time when the amount of residual image is reduced to a threshold value or less or the time when the rate of change in the amount of residual image is reduced to a threshold value or less. Therefore, the influence of the residual image on the first correction image CP1 selected by the selection unit 83 is suppressed.

FIG. 12 illustrates an aspect in which six first correction images CP1 are acquired immediately before the X-ray imaging. Numbers 1 to 6 are given in order of time in order to distinguish the six first correction images CP1. In the example illustrated in FIG. 12, the first correction images CP1 acquired after the predetermined time T has elapsed from the time when the immediately preceding X-ray imaging ended are "3" to "6". Among them, the first correction image CP1 of "6" is excluded because it is affected by the irradiation with the X-rays. Therefore, in the example illustrated in FIG. 12, the selection unit 83 selects three first correction images CP1 of "3" to "5" as the averaging target. The selection unit 83 supplies information of the selected averaging target to the offset correction unit 85.

In FIG. 6, the calibration image acquisition unit 84 includes a second correction image acquisition unit 84A and a third correction image acquisition unit 84B. The calibration image acquisition unit 84 acquires a calibration image in a state in which no X-rays are emitted during calibration such as in a case in which the electronic cassette 13 is started up or during maintenance. As illustrated in FIG. 7, the calibration image is acquired before the X-ray imaging and the acquisition of the first correction image CP1. For example, calibration is automatically performed in a case in which the electronic cassette 13 is started up, regardless of the operation of the operator. In addition, the calibration may be performed according to the operation of the operator.

The calibration images include a second correction image CP2 and a third correction image CP3. The second correction image acquisition unit 84A performs a second correction image acquisition process of acquiring the second correction image CP2 using the same reading method (that is, the binning reading method) as that used for the first correction image CP1. The third correction image acquisition unit 84B performs a third correction image acquisition process of acquiring the third correction image CP3 using the same reading method (that is, the sequential reading method) as that used for the X-ray image XP.

The third correction image acquisition unit 84B drives the reading unit 45 using the same driving method as the X-ray image generation unit 80 except that the reading unit 45 is driven in a state in which no X-rays are emitted.

The second correction image acquisition unit 84A drives the reading unit 45 to acquire the second correction image CP2 in a state in which no X-rays are emitted immediately before the third correction image acquisition unit 84B acquires the third correction image CP3. In this embodiment, the number of second correction images CP2 acquired by the second correction image acquisition unit 84A is one. The second correction image acquisition unit 84A drives the reading unit 45 using the same driving method as the first correction image acquisition unit 81 except that the number of acquired second correction images CP2 is different from the number of acquired first correction images CP1.

The second correction image acquisition unit 84A and the third correction image acquisition unit 84B store the acquired second and third correction images CP2 and CP3 in the correction image storage unit 87, respectively.

Figure 13:
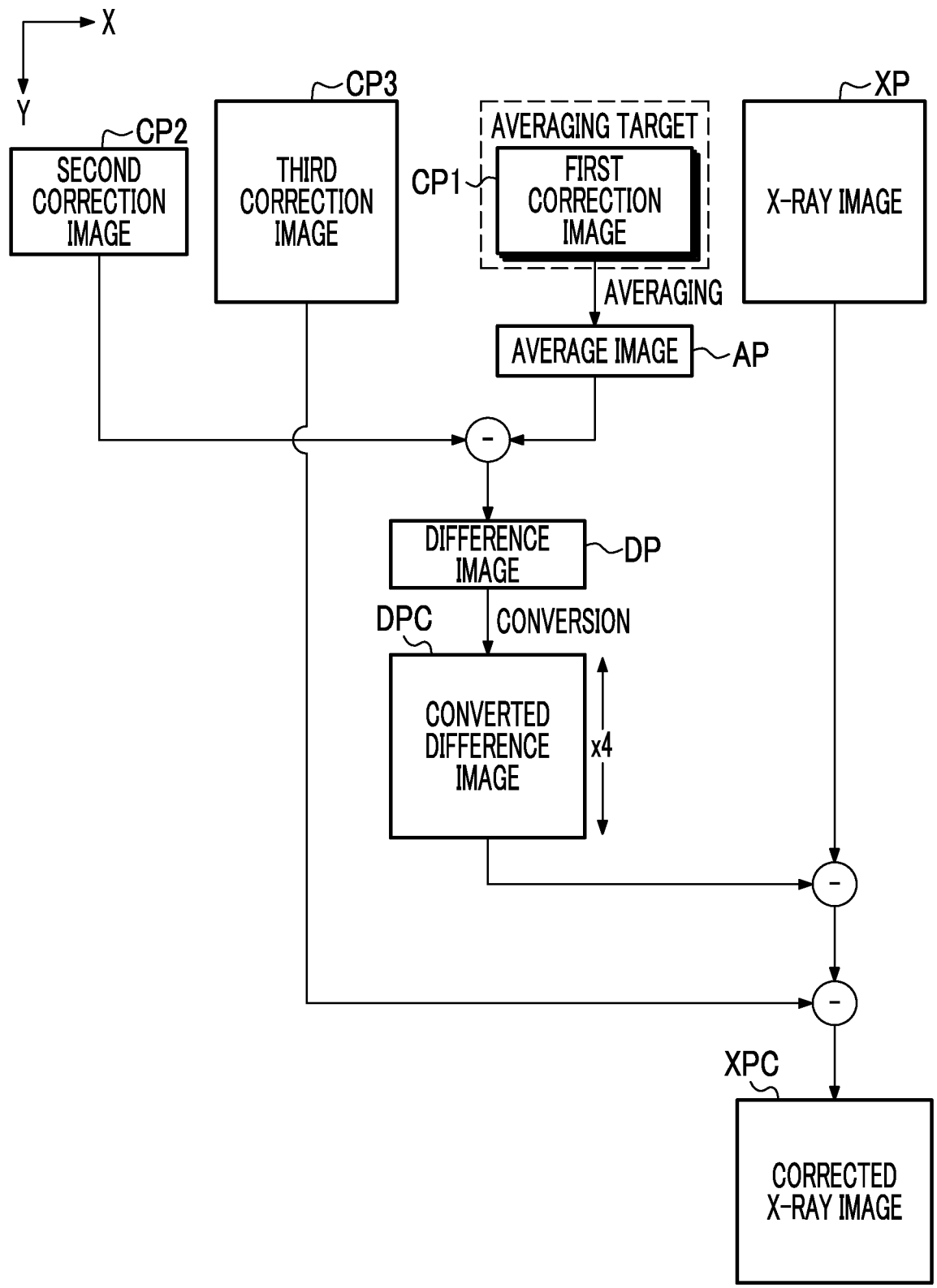
FIG. 13 is a diagram illustrating a correction process.

FIG. 13 illustrates the outline of offset correction by the offset correction unit 85. The offset correction unit 85 performs a correction process of correcting the X-ray image XP on the basis of the first correction image CP1, the second correction image CP2, and the third correction image CP3.

As illustrated in FIG. 6, the offset correction unit 85 includes an average image generation unit 90, a difference image generation unit 91, a conversion unit 92, and a subtraction unit 93. The average image generation unit 90 averages a plurality of first correction images CP1 included in the averaging targets selected by the selection unit 83 to generate an average image AP. Specifically, the average image generation unit 90 acquires the plurality of first correction images CP1 included in the averaging targets from the correction image storage unit 87 and averages the added pixel signals AS of the plurality of acquired first correction images CP1 for each corresponding addition pixel. In the average image AP generated by the averaging, random noise is suppressed more than in the first correction image CP1. The average image generation unit 90 stores the generated average image AP in the correction image storage unit 87.

The difference image generation unit 91 acquires the average image AP and the second correction image CP2 from the correction image storage unit 87 and generates a difference image DP between the acquired average image AP and second correction image CP2. For example, the difference image generation unit 91 subtracts the second correction image CP2 from the average image AP for each corresponding addition pixel to generate the difference image DP. The difference image generation unit 91 stores the generated difference image DP in the correction image storage unit 87.

The conversion unit 92 acquires the difference image DP from the correction image storage unit 87 and performs at least one of the accumulation time multiplication process or the enlargement and reduction process for adjusting an image size to the X-ray image XP on the acquired difference image DP. In this embodiment, both the multiplication process and the enlargement and reduction process are performed on the difference image DP.

The conversion unit 92 performs a multiplication process of multiplying each pixel value of the difference image DP by the ratio (AT1/AT2) of the accumulation period AT1 in the X-ray imaging to the accumulation period AT2 in the acquisition of the first correction image and the second correction image as a coefficient. In addition, the conversion unit 92 performs an enlargement process of enlarging the difference image DP in the direction (the Y direction in this embodiment) in which the image has been reduced by the binning reading to adjust the image size of the difference image DP to the image size of the X-ray image XP (see FIG. 13). This enlargement process is performed, for example, by a complement process.

In addition, the conversion unit 92 multiplies a conversion coefficient corresponding to the difference between the reading method (sequential reading method) in the X-ray imaging and the reading method (binning reading method) in the acquisition of the first correction image and the second correction image. In the sequential reading method, the charge corresponding to one pixel is converted into a pixel signal by the signal processing circuit 42. In contrast, in the binning reading method, the charge output from a plurality of pixels is added and converted into a pixel signal by the signal processing circuit 42. The conversion characteristics of the signal processing circuit 42 converting the charge into the pixel signal are not necessarily linear. For example, the added pixel signal based on the charge corresponding to four pixels is likely to deviate from a value that is four times as large as the pixel signal based on the charge corresponding to one pixel. Therefore, the conversion unit 92 multiplies each pixel value of the difference image DP by a conversion coefficient for correcting the nonlinearity of the conversion characteristics of the signal processing circuit 42. The conversion unit 92 stores a converted difference image DPC obtained by converting the difference image DP in the correction image storage unit 87.

The subtraction unit 93 acquires the X-ray image XP from the X-ray image storage unit 86 and acquires the converted difference image DPC and the third correction image CP3 from the correction image storage unit 87. The subtraction unit 93 performs a subtraction process of subtracting each of the converted difference image DPC and the third correction image CP3 from the acquired X-ray image XP. The subtraction unit 93 stores a corrected X-ray image XPC obtained as a result of the subtraction process in the X-ray image storage unit 86. For example, the corrected X-ray image XPC is displayed on the display 14B (see FIG. 1).

Figure 14:
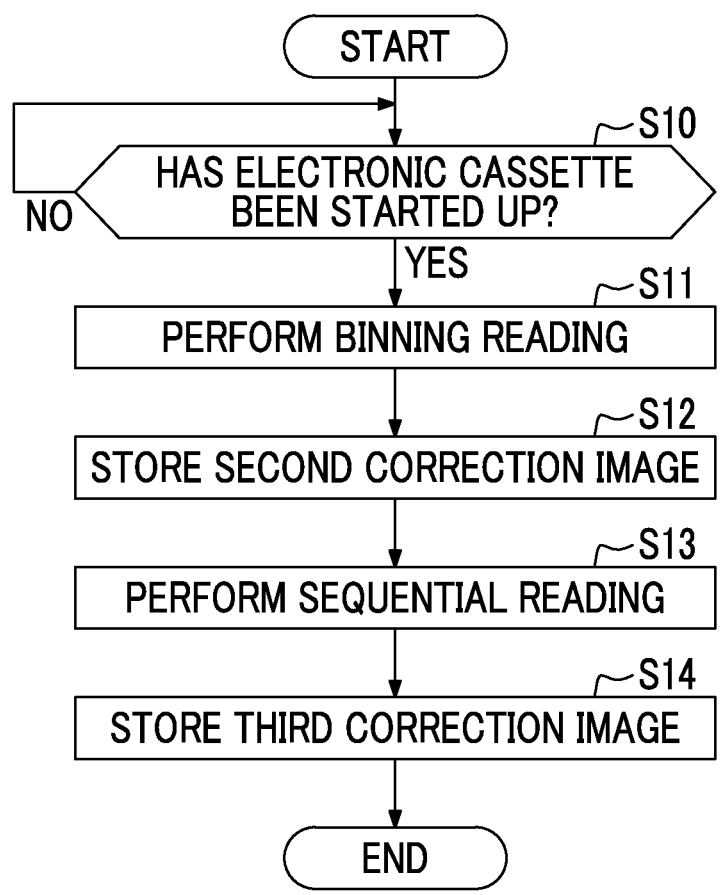
FIG. 14 is a flowchart illustrating a processing procedure in calibration.
Figure 15:
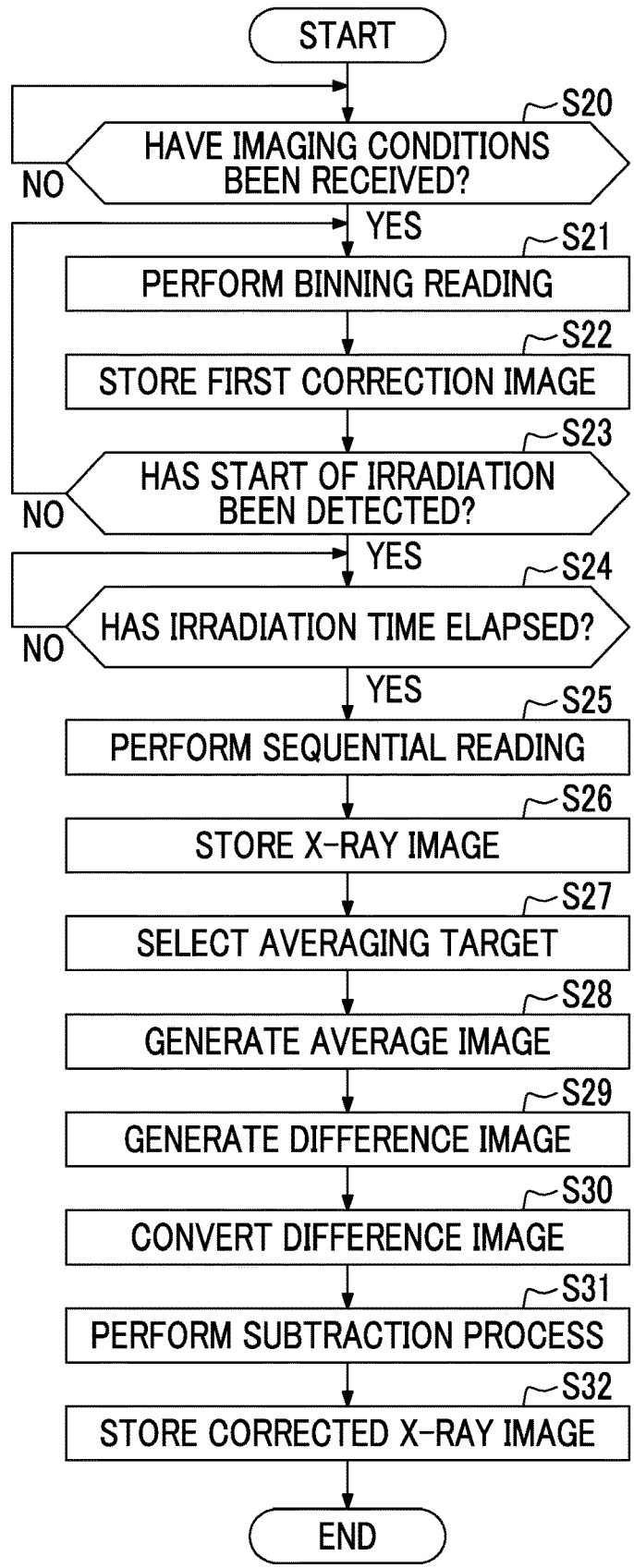
FIG. 15 is a flowchart illustrating a processing procedure in X-ray imaging.

Next, the operation of the X-ray imaging system 2 having the above-mentioned configuration will be described with reference to flowcharts illustrated in FIGS. 14 and 15. FIG. 14 is a flowchart illustrating a processing procedure in calibration. FIG. 15 is a flowchart illustrating a processing procedure in X-ray imaging.

First, the control unit 43 of the electronic cassette 13 determines whether or not the electronic cassette 13 has been started up by the pressure of the power switch 33 (see FIG. 3) of the electronic cassette 13 by the operator (Step S10). In a case in which the control unit 43 determines that the electronic cassette 13 has been started up (Step S10: YES), the second correction image acquisition unit 84A drives the reading unit 45 using the binning reading method to acquire the second correction image CP2 (Step S11). The second correction image acquisition unit 84A stores the acquired second correction image CP2 in the correction image storage unit 87 (Step S12).

Then, the third correction image acquisition unit 84B drives the reading unit 45 using the sequential reading method to acquire the third correction image CP3 (Step S13). The third correction image acquisition unit 84B stores the acquired third correction image CP3 in the correction image storage unit 87 (Step S14). In this way, the calibration operation ends.

Next, in the X-ray imaging, the operator sets the subject at the imaging position of the upright imaging stand 15 or the decubitus imaging stand 16 and adjusts the position of the electronic cassette 13. In addition, the operator adjusts the position of the X-ray source 10 and the size of the irradiation field according to the position of the electronic cassette 13 and the size of an imaging part of the subject. Then, the operator sets imaging conditions in the radiation source control device 11 and the console 14. The imaging conditions set in the console 14 are transmitted to the electronic cassette 13.

The control unit 43 of the electronic cassette 13 waits for the imaging conditions transmitted from the console 14 (Step S20). In a case in which the control unit 43 receives the imaging conditions from the console 14 through the communication I/F 44 (Step S20: YES), the first correction image acquisition unit 81 drives the reading unit 45 using the binning reading method to acquire the first correction image CP1 (Step S21). The first correction image acquisition unit 81 stores the acquired first correction image CP1 in the correction image storage unit 87 (Step S22).

The irradiation start detection unit 82 operates during the binning reading operation to detect the start of irradiation with X-rays on the basis of the added pixel signal AS obtained during the binning reading (Step S23). In a case in which the irradiation start detection unit 82 does not detect the start of irradiation with X-rays (Step S23: NO), the process in Steps S21 and S22 is repeated.

In the X-ray imaging, the operator presses the irradiation switch 12 halfway to instruct preparation for imaging. In a case in which the irradiation switch 12 is pressed halfway, a warm-up instruction signal is issued to the high voltage generator 21, and the warm-up of the X-ray source 10 is started. Then, in a case in which the operator fully presses the irradiation switch 12, X-rays are emitted from the X-ray source 10 to the subject.

In a case in which the irradiation start detection unit 82 detects the start of irradiation with X-rays (Step S23: YES), the X-ray image generation unit 80 stops the binning reading and starts measuring the irradiation time using the timer 73. Then, the pixel region 40 is changed to a charge accumulation state and accumulates charge corresponding to the amount of X-rays emitted through the subject. The X-ray image generation unit 80 determines whether or not the irradiation time included in the imaging conditions has elapsed (Step S24).

In a case in which the X-ray image generation unit 80 determines that the irradiation time has elapsed (Step S24: YES), it drives the reading unit 45 using the sequential reading method to generate the X-ray image XP (Step S25). The X-ray image generation unit 80 stores the generated X-ray image XP in the X-ray image storage unit 86 (Step S26).

Then, the selection unit 83 selects the first correction images CP1 as the averaging target from a plurality of first correction images CP1 acquired immediately before the X-ray imaging (Step S27). Specifically, as described above, the selection unit 83 selects, as the averaging target, the first correction image CP1 acquired after the predetermined time T has elapsed since the time when the immediately preceding X-ray imaging ended and excludes the first correction image CP1 most immediately before the X-ray imaging. The average image generation unit 90 averages a plurality of first correction images CP1 included in the averaging targets selected by the selection unit 83 to generate the average image AP (Step S28).

Then, the difference image generation unit 91 generates the difference image DP between the average image AP and the second correction image CP2 (Step S29). The conversion unit 92 performs the accumulation time multiplication process, the enlargement and reduction process for adjusting the image size to the X-ray image XP, and the process of multiplying a conversion coefficient corresponding to the difference between the reading methods on the difference image DP to generate the converted difference image DPC (Step S30). Then, the subtraction unit 93 performs the subtraction process of subtracting each of the converted difference image DPC and the third correction image CP3 from the X-ray image XP to generate the corrected X-ray image XPC (Step S31). The subtraction unit 93 stores the generated corrected X-ray image XPC in the X-ray image storage unit 86 (Step S32).

Figure 16:
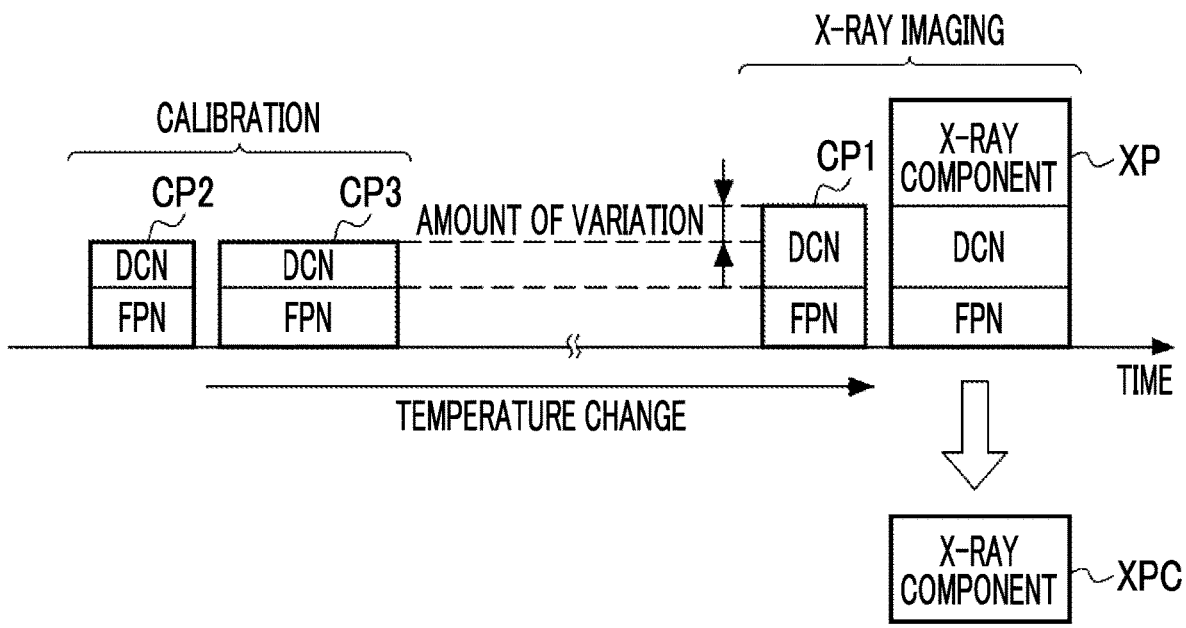
FIG. 16 is a schematic diagram illustrating noise components included in an X-ray image and a correction image.

FIG. 16 is a schematic diagram illustrating noise components included in the X-ray image XP, the first correction image CP1, the second correction image CP2, and the third correction image CP3. Since the first correction image CP1, the second correction image CP2, and the third correction image CP3 are acquired in a state in which no X-rays are emitted, they mainly include dark current noise (DCN) and fixed pattern noise (FPN).

The DCN is mainly caused by a dark current that is generated in each pixel 50 due to heat. The FPN is mainly caused by a variation in the characteristics of the integrator 60 connected to each signal line 54. Since the DCN is caused by heat, it varies due to a temperature change. In contrast, since the FPN is caused by the characteristics of the integrator 60, it is constant regardless of a temperature change.

The X-ray image XP includes the DCN and the FPN in addition to an X-ray component caused by irradiation with X-rays.

The calibration is performed, for example, in a case in which the electronic cassette 13 is started up. Therefore, in some cases, it takes a long time from the calibration to the X-ray imaging. In a case in which the temperature changes during the period, the DCN changes. In particular, since the electronic cassette 13 is portable and small in size, it has a small heat capacity. Therefore, the electronic cassette 13 is likely to be affected by an environmental temperature change. Further, since the electronic cassette 13 periodically detects the start of irradiation, it consumes a large amount of power and generates heat. Therefore, a temperature change is likely to occur. As described above, in the electronic cassette 13, the amount of variation in DCN is large. Therefore, it is difficult to perform offset correction on the X-ray image XP with high accuracy using only the correction image acquired during the calibration.

In the electronic cassette 13 according to this embodiment, the X-ray image XP is corrected on the basis of the average image AP of the plurality of first correction images CP1 acquired in a state in which no X-rays are emitted immediately before the X-ray imaging including the X-ray image generation process. Therefore, it is possible to perform offset correction on the X-ray image XP with high accuracy.

Further, in the electronic cassette 13 according to this embodiment, the pixel signal is read from the pixel region 40 a plurality of times by the binning reading to acquire a plurality of first correction images CP1 in a state in which no X-rays are emitted immediately before the X-ray imaging. Therefore, it is possible to shorten a time lag immediately before the X-ray imaging.

Further, in the electronic cassette 13 according to this embodiment, the X-ray image XP is corrected on the basis of the average image obtained by selecting an averaging target from a plurality of first correction images CP1 according to the time elapsed since the immediately preceding X-ray imaging and averaging the selected first correction images CP1. Therefore, it is possible to improve the accuracy of offset correction and to suppress the influence of a residual image.

In addition, in the electronic cassette 13 according to this embodiment, the X-ray image XP is corrected on the basis of the difference image DP between the average image AP and the second correction image CP2. Since the difference image DP corresponds to the amount of variation in DCN from the calibration, it is possible to accurately correct the amount of variation in DCN.

Further, in the electronic cassette 13 according to this embodiment, the X-ray image XP is corrected on the basis of the third correction image CP3 and the difference image DP. Since the third correction image CP3 is a correction image acquired by the same reading method as the X-ray image XP, the accuracy of offset correction is further improved.

Furthermore, in the electronic cassette 13 according to this embodiment, the second correction image CP2 is acquired immediately before the third correction image CP3 is acquired. With this configuration, the second correction image CP2 and the third correction image CP3 are acquired at the same reading timing as the first correction image CP1 and the X-ray image XP acquired during the X-ray imaging. Therefore, the accuracy of offset correction is further improved.

Further, in the electronic cassette 13 according to this embodiment, the accumulation time multiplication process or the enlargement and reduction process for adjusting the image size to the X-ray image XP and the process of multiplying a conversion coefficient corresponding to the difference between the reading methods are performed on the difference image DP. Therefore, the accuracy of offset correction is further improved.

Second Embodiment

Next, a second embodiment of the present disclosure will be described. The second embodiment differs from the first embodiment in the averaging target selection process of the selection unit 83. The other configurations of an X-ray imaging system according to the second embodiment are the same as the configurations of the X-ray imaging system 2 according to the first embodiment.

Figure 17:
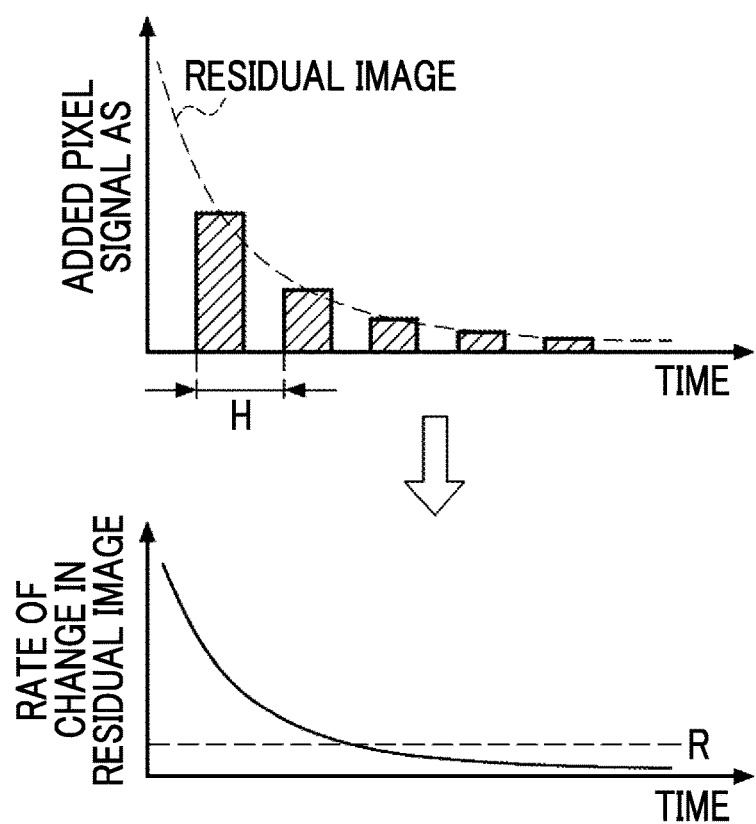
FIG. 17 is a diagram illustrating a selection process of a selection unit according to a second embodiment.

In this embodiment, similarly to the irradiation start detection unit 82, the selection unit 83 monitors the signal value of the added pixel signal AS read by the binning reading to select the first correction image CP1 as the averaging target. Specifically, as illustrated in FIG. 17, the selection unit 83 calculates the rate of change in the residual image over time on the basis of the signal value of the added pixel signal AS. Then, the selection unit 83 selects, as the averaging target, the first correction image CP1 acquired during the period for which the rate of change in the residual image is equal to or less than a predetermined value R.

As such, in this embodiment, as in the first embodiment, the first correction image CP1 is selected on the basis of the rate of change in the residual image which has been calculated not on the basis of the time elapsed since the time when the immediately preceding X-ray imaging ended, but on the basis of the added pixel signal AS. Therefore, in this embodiment, even in a case in which the characteristics of the residual image are different, it is possible to select the first correction image CP1 that is less affected by the residual image.

Further, the selection unit 83 may calculate the rate of change in the residual image on the basis of the maximum value of the added pixel signals AS obtained through a plurality of signal lines 54 for each pixel row. Furthermore, the selection unit 83 may calculate the rate of change in the residual image on the basis of an average value or a sum, instead of the maximum value of the added pixel signals AS for each pixel row. The selection unit 83 may calculate the rate of change in the residual image over time on the basis of the first correction image CP1.

Third Embodiment

Next, a third embodiment of the present disclosure will be described. The third embodiment differs from the first embodiment in the reading method of the second correction image acquisition unit 84A and the third correction image acquisition unit 84B. The other configurations of an X-ray imaging system according to the third embodiment are the same as the configurations of the X-ray imaging system 2 according to the first embodiment.

In this embodiment, the second correction image acquisition unit 84A drives the reading unit 45 in a state in which the gates (the gate electrodes of the TFTs 52) of all of the pixels 50 included in the pixel region 40 are turned off. Similarly, the third correction image acquisition unit 84B drives the reading unit 45 in a state in which the gates of all of the pixels 50 included in the pixel region 40 are turned off. That is, the second correction image acquisition unit 84A and the third correction image acquisition unit 84B drive the reading unit 45 using the same reading method as in the first embodiment except that no gate pulses are applied from the gate driver 41 to the scanning lines 53.

Figure 18:
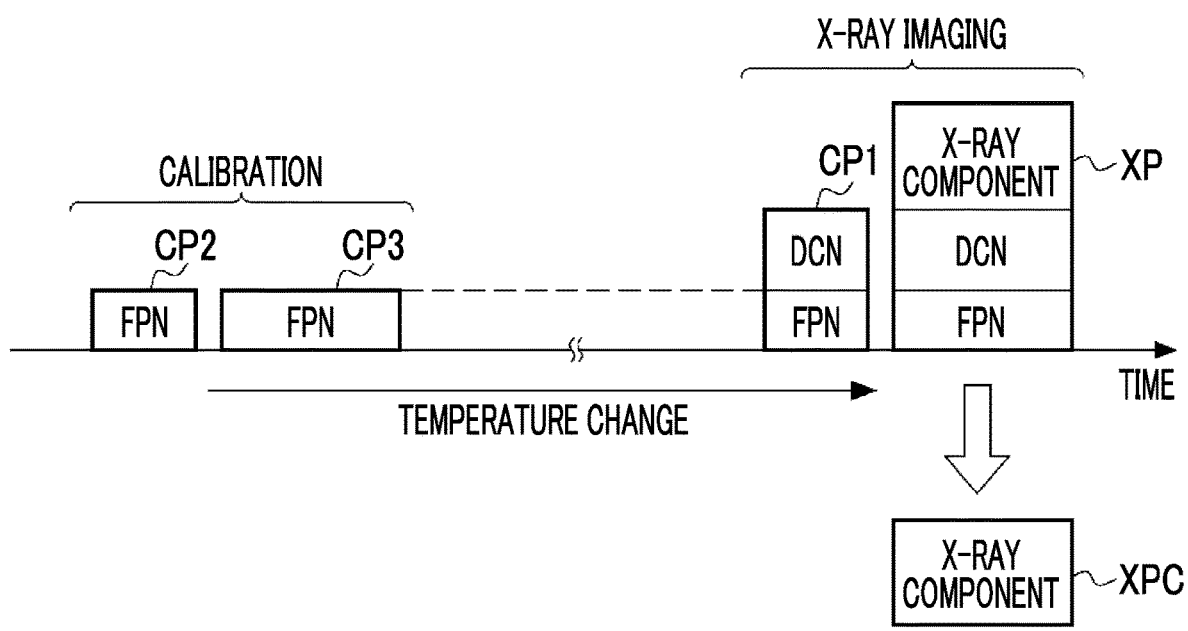
FIG. 18 is a schematic diagram illustrating noise components included in an X-ray image and a correction image acquired in the second embodiment.

FIG. 18 is a schematic diagram illustrating noise components included in the X-ray image XP, the first correction image CP1, the second correction image CP2, and the third correction image CP3 acquired in this embodiment. In this embodiment, during calibration, the second correction image CP2 and the third correction image CP3 are acquired in a state in which the gates of the pixels 50 are turned off. Therefore, the second correction image CP2 and the third correction image CP3 do not include DCN generated in the pixels 50 and mainly include FPN. Therefore, in this embodiment, the difference image DP between the average image AP and the second correction image CP2 is not the amount of variation in DCN, but is DCN.

In addition, in this embodiment, the offset correction unit 85 performs the same correction process (see FIG. 13) as in the first embodiment to obtain the same corrected X-ray image XPC as in the first embodiment.

Other Modification Examples

In each of the above-described embodiments, the reading unit 45 is driven by the binning reading method to acquire the first correction image CP1 and the second correction image CP2. However, the reading unit 45 may be driven by the sequential reading method to acquire the first correction image CP1 and the second correction image CP2. In this case, the accumulation time in a case in which the first correction image CP1 and the second correction image CP2 are acquired may be shorter than the accumulation time in a case in which the X-ray image XP and the third correction image CP3 are acquired. That is, the first correction image CP1 and the second correction image CP2 may be acquired in a shorter accumulation time than the X-ray image XP or by the binning reading.

Further, in each of the above-described embodiments, the second correction image acquisition unit 84A acquires one second correction image CP2. However, the second correction image acquisition unit 84A may acquire a plurality of second correction images CP2 similarly to the first correction images CP1. In this case, a difference image between an average image obtained by averaging the plurality of second correction images CP2 and the average image AP may be used as the difference image DP.

Further, in each of the above-described embodiments, only the offset correction is performed as the correction process. However, in addition to the offset correction, for example, the following processes may be performed: gain correction for correcting a variation in the sensitivity of the image detection unit 30 to irradiation with X-rays; and defective pixel correction.

Further, the technology of the present disclosure is not limited to X-rays and can be applied to a system that captures the image of the subject using other kinds of radiation such as γ-rays.

In each of the above-described embodiments, for example, the following various processors can be used as a hardware structure of processing units performing various processes, such as the X-ray image generation unit 80, the first correction image acquisition unit 81, the irradiation start detection unit 82, the selection unit 83, the calibration image acquisition unit 84, and the offset correction unit 85.

The various processors include, for example, a CPU, a programmable logic device (PLD), a dedicated electric circuit. As is well known, the CPU is a general-purpose processor that executes software (program) to function as various processing units. The PLD is a processor whose circuit configuration can be changed after manufacture, such as a field programmable gate array (FPGA). The dedicated electric circuit is a processor that has a dedicated circuit configuration designed to perform a specific process, such as an application specific integrated circuit (ASIC).

One processing unit may be configured by one of the various processors or a combination of two or more processors of the same type or different types (for example, a combination of a plurality of FPGAs and a combination of a CPU and an FPGA). Further, a plurality of processing units may be configured by one processor. A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one IC chip is used. A representative example of this aspect is a system-on-chip (SoC). As such, various processing units are configured by using one or more of the various processors as the hardware structure.

In addition, specifically, an electric circuit (circuitry) obtained by combining circuit elements, such as semiconductor elements, is used as the hardware structure of the various processors.

The technology of the present disclosure is not limited to each of the above-described embodiments and may adopt various configurations without departing from the spirit and scope of the present disclosure. Furthermore, the technology of the present disclosure extends to a computer-readable storage medium that non-temporarily stores the program, in addition to the program.

What is claimed is:

1. A radiographic image detection device comprising:
   a pixel region in which a plurality of pixels detecting radiation are arranged;
   a reading circuit that reads a pixel signal from the pixel region; and
   at least one processor,
   wherein the processor performs:
   a radiographic image generation process of reading the pixel signal from the pixel region in a state in which the radiation is emitted to generate a radiographic image;
   a first correction image acquisition process of reading the pixel signal from the pixel region a plurality of times to acquire a plurality of first correction images in a shorter accumulation time than the radiographic image or using binning reading in a state in which the radiation is not emitted immediately before radiography including the radiographic image generation process;
   a selection process of selecting, as an averaging target, a subset of the plurality of first correction images comprising at least two or more of the plurality of first correction images according to a time elapsed since immediately preceding radiography or an amount of variation in a residual image based on the first correction image; and
   a correction process of correcting the radiographic image on the basis of an average image obtained by averaging the first correction images selected as the averaging target,
   wherein, in the selection process, the processor selects, as the averaging target, the first correction image acquired for a period for which the time elapsed since the immediately preceding radiography is equal to or greater than a predetermined value among the plurality of first correction images acquired by the first correction image acquisition process.

2. The radiographic image detection device according to claim 1, wherein, in the selection process:
   the processor calculates a rate of change in the residual image over time on the basis of the plurality of first correction images acquired by the first correction image acquisition process, and the processor selects, as the averaging target, the first correction image acquired for a period for which the rate of change is equal to or less than a predetermined value.

3. The radiographic image detection device according to claim 1,
wherein the processor performs a second correction image acquisition process of acquiring a second correction image using the same reading method as that used for the first correction image in a state in which the radiation is not emitted before the first correction image is acquired by the first correction image acquisition process, and
in the correction process, the processor corrects the radiographic image on the basis of a difference image between the average image and the second correction image.

4. The radiographic image detection device according to claim 3,
wherein the processor performs a third correction image acquisition process of acquiring a third correction image using the same reading method as that used for the radiographic image in a state in which the radiation is not emitted before the first correction image is acquired by the first correction image acquisition process, and
in the correction process, the processor corrects the radiographic image on the basis of the third correction image and the difference image.

5. The radiographic image detection device according to claim 4,
wherein the processor acquires the second correction image using the second correction image acquisition process immediately before the third correction image is acquired by the third correction image acquisition process.

6. The radiographic image detection device according to claim 4, wherein, in the correction process:
the processor subtracts the difference image and the third correction image from the radiographic image after performing, on the difference image:
an accumulation time multiplication process or an enlargement and reduction process for adjusting an image size to the radiographic image and
a process of multiplying a conversion coefficient corresponding to a difference between the reading methods.

7. The radiographic image detection device according to claim 4,
wherein the processor performs the reading in a state in which gates of the plurality of pixels are turned off to generate the second correction image and the third correction image, and performs the reading in a state in which the gates of the plurality of pixels are turned on to generate the first correction image.

8. A method for operating a radiographic image detection device including a pixel region in which a plurality of pixels detecting radiation are arranged and a reading unit that reads a pixel signal from the pixel region, the method comprising:
a radiographic image generation step of reading the pixel signal from the pixel region in a state in which the radiation is emitted to generate a radiographic image;
a first correction image acquisition step of reading the pixel signal from the pixel region a plurality of times to acquire a plurality of first correction images in a shorter accumulation time than the radiographic image or using binning reading in a state in which the radiation is not emitted immediately before radiography including the radiographic image generation step;
a selection step of selecting, as an averaging target, a subset of the plurality of first correction images comprising at least two or more of the plurality of first correction images according to a time elapsed since immediately preceding radiography or an amount of variation in a residual image based on the first correction image; and
a correction step of correcting the radiographic image on the basis of an average image obtained by averaging the first correction images selected as the averaging target,
wherein, in the selection step, as the averaging target, the first correction image acquired for a period for which the time elapsed since the immediately preceding radiography is equal to or greater than a predetermined value is selected among the plurality of first correction images acquired in the first correction image acquisition step.

9. A non-transitory computer-readable storage medium storing an operation program for operating a radiographic image detection device comprising a pixel region in which a plurality of pixels detecting radiation are arranged, a reading unit that reads a pixel signal from the pixel region, and at least one processor, the operation program causing the processor to perform:
a radiographic image generation process of reading the pixel signal from the pixel region in a state in which the radiation is emitted to generate a radiographic image;
a first correction image acquisition process of reading the pixel signal from the pixel region a plurality of times to acquire a plurality of first correction images in a shorter accumulation time than the radiographic image or using binning reading in a state in which the radiation is not emitted immediately before radiography including the radiographic image generation process;
a selection process of selecting, as an averaging target, a subset of the plurality of first correction images comprising at least two or more of the plurality of first correction images according to a time elapsed since immediately preceding radiography or an amount of variation in a residual image based on the first correction image; and
a correction process of correcting the radiographic image on the basis of an average image obtained by averaging the first correction images selected as the averaging target,
wherein, in the selection process, the processor selects, as the averaging target, the first correction image acquired for a period for which the time elapsed since the immediately preceding radiography is equal to or greater than a predetermined value among the plurality of first correction images acquired by the first correction image acquisition process.

* * * * *